(12) United States Patent
Hsieh et al.

(10) Patent No.: US 10,864,381 B2
(45) Date of Patent: Dec. 15, 2020

(54) THERAPEUTIC LIGHT-EMITTING MODULE

(71) Applicant: EPISTAR CORPORATION, Hsinchu (TW)

(72) Inventors: Min-Hsun Hsieh, Hsinchu (TW); Jai-Tai Kuo, Hsinchu (TW); Chang-Hseih Wu, Hsinchu (TW); Tzu-Hsiang Wang, Hsinchu (TW); Chi-Chih Pu, Hsinchu (TW)

(73) Assignee: EPISTAR CORPORATION, Hsinchu (TW)

( * ) Notice: Subject to any disclaimer, the term of this patent is extended or adjusted under 35 U.S.C. 154(b) by 0 days.

(21) Appl. No.: 16/803,415

(22) Filed: Feb. 27, 2020

(65) Prior Publication Data

US 2020/0197719 A1    Jun. 25, 2020

Related U.S. Application Data

(63) Continuation of application No. 15/709,118, filed on Sep. 19, 2017, now Pat. No. 10,596,388.

(60) Provisional application No. 62/397,526, filed on Sep. 21, 2016.

(51) Int. Cl.
| | |
|---|---|
| *A61N 5/06* | (2006.01) |
| *A61B 5/00* | (2006.01) |
| *H01L 25/075* | (2006.01) |
| *H01L 27/15* | (2006.01) |
| *A61B 17/00* | (2006.01) |

(52) U.S. Cl.
CPC ............ *A61N 5/062* (2013.01); *A61B 5/0059* (2013.01); *A61N 5/0616* (2013.01); *H01L 25/0756* (2013.01); *H01L 27/15* (2013.01); *A61B 2017/00057* (2013.01); *A61N 2005/0632* (2013.01); *A61N 2005/0652* (2013.01); *A61N 2005/0658* (2013.01)

(58) Field of Classification Search
CPC .................................................. A61N 5/0616
See application file for complete search history.

(56) References Cited

U.S. PATENT DOCUMENTS

| | | |
|---|---|---|
| 5,358,503 A | 10/1994 | Bertwell et al. |
| 5,800,478 A | 9/1998 | Chen et al. |
| 6,290,713 B1 | 9/2001 | Russell |
| 6,331,111 B1 | 12/2001 | Cao |
| 6,443,978 B1 | 9/2002 | Zharov |
| 6,645,230 B2 | 11/2003 | Whitehurst |
| 7,070,611 B2 | 7/2006 | Biel |
| 7,081,128 B2 | 7/2006 | Hart et al. |
| 7,195,605 B1 * | 3/2007 | White ............... A61F 13/066 602/21 |
| 8,177,383 B2 | 5/2012 | Reuben |
| 8,372,128 B2 | 2/2013 | Reuben |

(Continued)

FOREIGN PATENT DOCUMENTS

WO    WO-2013190467 A2    12/2013

*Primary Examiner* — John P. Dulka
(74) *Attorney, Agent, or Firm* — Patterson + Sheridan, LLP

(57) ABSTRACT

A light-emitting module includes a housing, a flexible film, and a protection portion. The housing includes a plurality of light-emitting units arranged in a matrix configuration and at least a switch electrically connected to at least one of the plurality of light-emitting units. The flexible film is detachably coupled to the housing. The protection portion covers the plurality of light-emitting units.

10 Claims, 15 Drawing Sheets

(56) References Cited

U.S. PATENT DOCUMENTS

| | | |
|---|---|---|
| 8,587,011 B2 | 11/2013 | Matsuda et al. |
| 8,723,195 B2 | 5/2014 | Ishizaki et al. |
| 8,760,295 B2 | 6/2014 | Forster |
| 9,370,449 B2 | 6/2016 | Anderson et al. |
| 9,437,628 B1 | 9/2016 | Ma et al. |
| 9,782,482 B2 | 10/2017 | Faupel et al. |
| 9,829,159 B2 | 11/2017 | McGowan et al. |
| 9,968,800 B2 | 5/2018 | Anderson et al. |
| 10,022,555 B2 | 7/2018 | Tapper et al. |
| 10,044,085 B2 | 8/2018 | Ma et al. |
| 2002/0195367 A1 | 12/2002 | Dotta |
| 2003/0165482 A1 | 9/2003 | Rolland et al. |
| 2004/0166146 A1 | 8/2004 | Holloway et al. |
| 2005/0254226 A1* | 11/2005 | Sawada ............... G01D 11/28 362/23.01 |
| 2006/0089686 A1 | 4/2006 | Streibich et al. |
| 2006/0173253 A1 | 8/2006 | Ganapathy et al. |
| 2006/0173514 A1 | 8/2006 | Biel et al. |
| 2006/0217787 A1 | 9/2006 | Olson et al. |
| 2007/0219605 A1 | 9/2007 | Yaroslaysky et al. |
| 2007/0233208 A1 | 10/2007 | Kurtz et al. |
| 2007/0239232 A1 | 10/2007 | Kurtz et al. |
| 2008/0004510 A1* | 1/2008 | Tanzawa ............... A61B 5/00 600/301 |
| 2008/0058907 A1 | 3/2008 | Reuben |
| 2008/0171957 A1 | 7/2008 | Connolly et al. |
| 2008/0174436 A1 | 7/2008 | Landt et al. |
| 2008/0215020 A1 | 9/2008 | Reeves et al. |
| 2008/0269849 A1 | 10/2008 | Lewis |
| 2009/0099499 A1 | 4/2009 | Persin et al. |
| 2009/0105791 A1 | 4/2009 | McGinnis et al. |
| 2009/0209896 A1 | 8/2009 | Selevan |
| 2010/0161009 A1 | 6/2010 | Forster |
| 2010/0179469 A1 | 7/2010 | Hammond et al. |
| 2010/0249560 A1 | 9/2010 | Levinson et al. |
| 2010/0318168 A1 | 12/2010 | Bighetti |
| 2011/0112490 A1 | 5/2011 | Vogel et al. |
| 2011/0176326 A1 | 7/2011 | Stephan |
| 2012/0001149 A1 | 1/2012 | Menon |
| 2012/0116485 A1 | 5/2012 | Burgmann |
| 2012/0165716 A1 | 6/2012 | Reuben |
| 2012/0303101 A1 | 11/2012 | Rogers et al. |
| 2013/0103123 A1 | 4/2013 | Khan et al. |
| 2013/0176732 A1 | 7/2013 | McGowan et al. |
| 2013/0193453 A1* | 8/2013 | Donofrio ............ H01L 25/0753 257/88 |
| 2013/0271278 A1 | 10/2013 | Duesterhoft et al. |
| 2014/0046278 A1 | 2/2014 | Eckstein et al. |
| 2014/0074010 A1 | 3/2014 | Veres et al. |
| 2014/0209943 A1 | 7/2014 | Yamamoto et al. |
| 2014/0277297 A1 | 9/2014 | Harris et al. |
| 2014/0319553 A1 | 10/2014 | Ye et al. |
| 2015/0018742 A1 | 1/2015 | Baumgartner |
| 2015/0032070 A1 | 1/2015 | Colby |
| 2015/0174304 A1 | 6/2015 | Askem et al. |
| 2015/0238774 A1 | 8/2015 | Anderson et al. |
| 2015/0290470 A1 | 10/2015 | Tapper et al. |
| 2016/0015962 A1 | 1/2016 | Shokoueinejad Maragheh et al. |
| 2016/0016001 A1 | 1/2016 | Loupis et al. |
| 2016/0114186 A1 | 4/2016 | Dobrinsky et al. |
| 2016/0143584 A1* | 5/2016 | Inagaki ............ A61B 5/02416 600/300 |
| 2016/0151210 A1 | 6/2016 | Jensen et al. |
| 2016/0166448 A1 | 6/2016 | Laje et al. |
| 2016/0208987 A1 | 7/2016 | McGowan et al. |
| 2016/0213711 A1 | 7/2016 | Palama et al. |
| 2016/0284956 A1 | 9/2016 | Ahn et al. |
| 2016/0296655 A1 | 10/2016 | Suschek |
| 2016/0338644 A1 | 11/2016 | Connor |
| 2016/0346565 A1 | 12/2016 | Rhodes et al. |
| 2017/0304557 A1 | 10/2017 | Chettiar et al. |
| 2017/0319715 A1 | 11/2017 | Towne et al. |
| 2018/0015298 A1 | 1/2018 | Iguchi et al. |
| 2018/0043043 A1* | 2/2018 | Spector ............... A61N 5/0624 |
| 2018/0043177 A1 | 2/2018 | Iguchi et al. |
| 2018/0043178 A1 | 2/2018 | Iguchi et al. |
| 2018/0056087 A1 | 3/2018 | Ribeiro et al. |
| 2018/0058641 A1 | 3/2018 | Takehara |
| 2018/0068986 A1 | 3/2018 | Yoo et al. |
| 2018/0078782 A1 | 3/2018 | Hsieh et al. |
| 2018/0085486 A1 | 3/2018 | Chen et al. |
| 2018/0110450 A1 | 4/2018 | Lamego et al. |
| 2018/0116877 A1 | 5/2018 | Ineichen |
| 2018/0161211 A1 | 6/2018 | Beckey |

\* cited by examiner

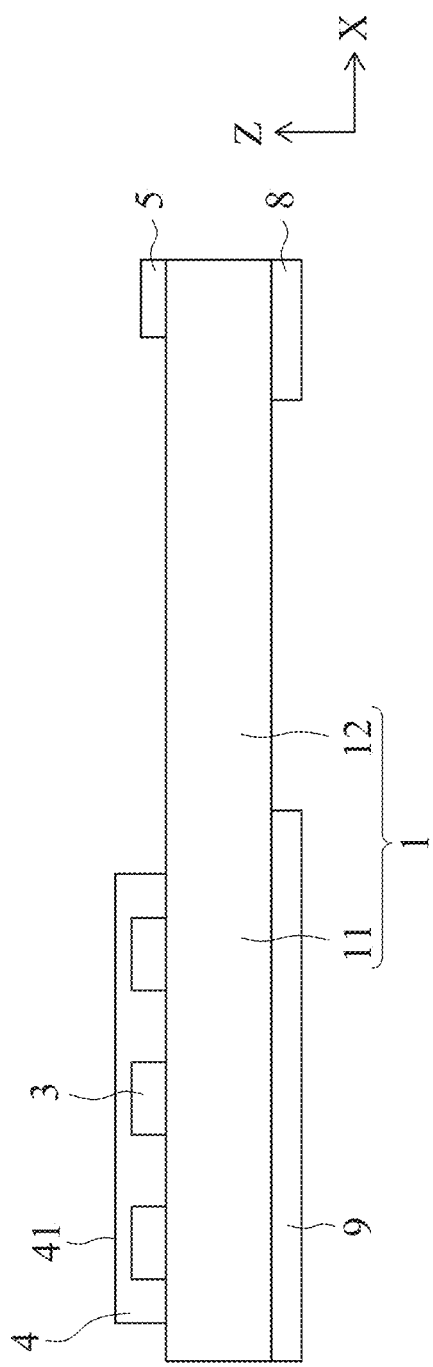
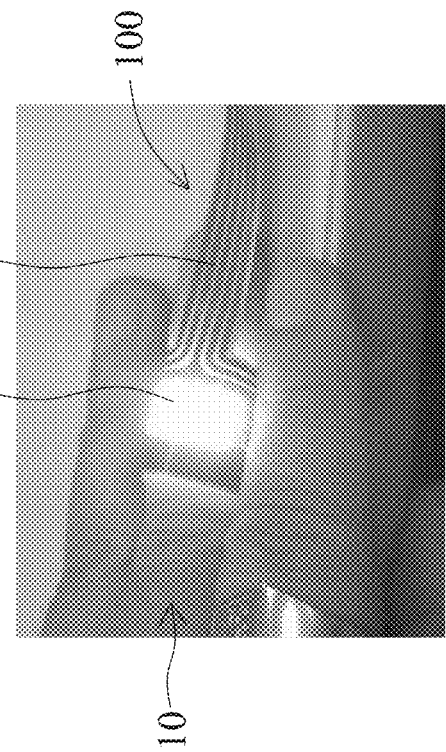

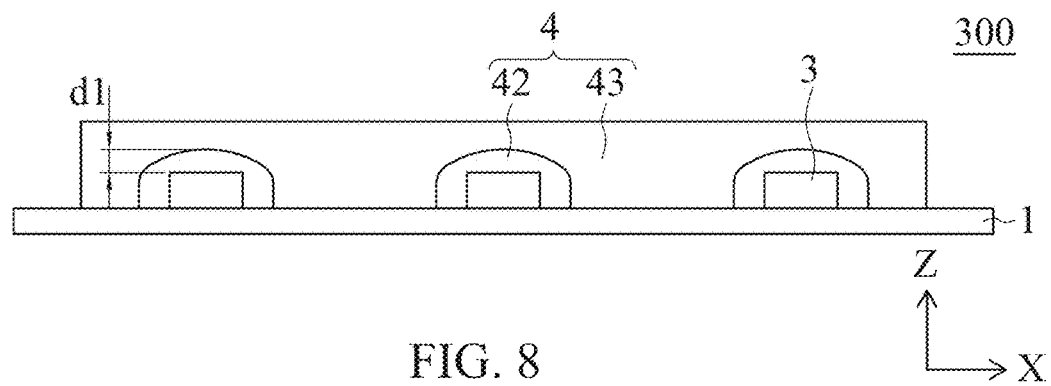
FIG. 8
| | Case A | Case B | Case C | Case D |
|---|---|---|---|---|
| Light-emitting angle | 120 | 130 | 140 | 150 |
FIG. 9A
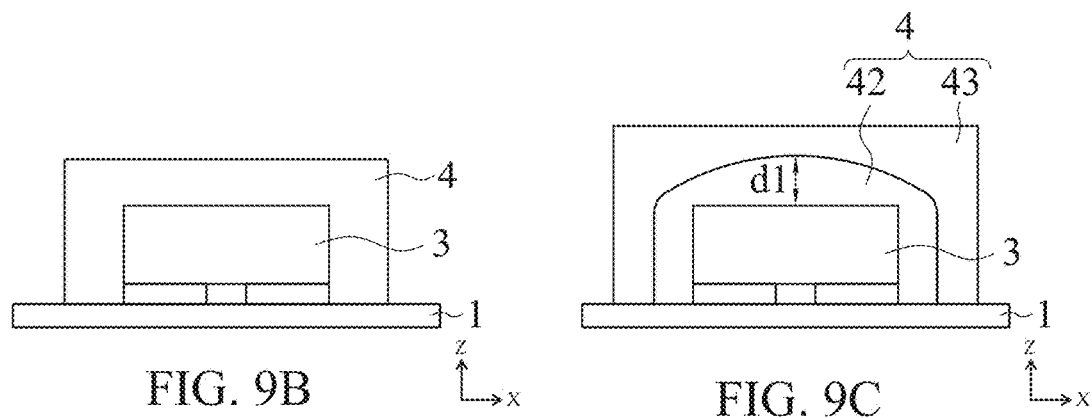
FIG. 9B    FIG. 9C
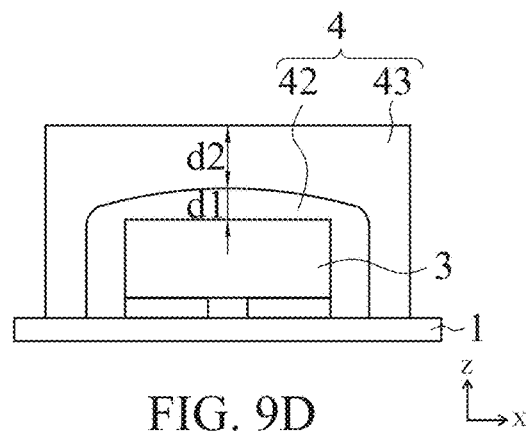
FIG. 9D

THERAPEUTIC LIGHT-EMITTING MODULE

RELATED APPLICATION

This application is a continuation of U.S. patent application Ser. No. 15/709,118, now U.S. Pat. No. 10,596,388, filed on Sep. 19, 2017, which claims the benefit of U.S. Provisional Application Ser. No. 62/397,526, filed on Sep. 21, 2016, which is incorporated herein by reference in its entirety.

TECHNICAL FIELD

The present disclosure relates to a light-emitting module and in particular to a light-emitting module used for photodynamic therapy.

DESCRIPTION OF THE RELATED ART

The known photodynamic therapy equipment includes a lamp connecting to a control module with multiple-function circuit, such as a timer for counting the therapy period, a current monitor for controlling the luminous intensity, a switch for driving all or some of the light-emitting units, a battery box for receiving the battery, and/or an AC adaptor for proving a suitable voltage/current to the lamp. The lamp is positioned approximately parallel to a treated area of a patient. The lamp needs to be separated from skin by a distance, for example, 2~5 cm, to achieve a uniform luminous intensity.

It is an object of the current disclosure to provide portable and bendable light photodynamic therapy equipment. According to one aspect of the present invention, the photodynamic therapy equipment of present invention is bendable and can conform to the skin to be treated or diagnosed, and the treated object can move easily during therapy.

SUMMARY OF THE DISCLOSURE

The following description illustrates embodiments and together with drawings to provide a further understanding of the disclosure described above.

A light-emitting module includes a housing, a flexible film, and a protection portion. The housing includes a plurality of light-emitting units arranged in a matrix configuration and at least a switch electrically connected to at least one of the plurality of light-emitting units. The flexible film is detachably coupled to the housing. The protection portion covers the plurality of light-emitting units.

BRIEF DESCRIPTION OF THE DRAWINGS

FIG. 1E shows a partial cross-sectional view of the light-emitting module in accordance with another embodiment of the present disclosure.

FIG. 2 shows an example the light-emitting module 100 wrapping the human's finger for therapy.

FIG. 8 shows a partial cross-sectional view of a light-emitting module in accordance with an embodiment of the present disclosure.

FIG. 9A is a table showing the light-emitting angles of light-emitting units in different cases.

FIGS. 9B~FIG. 9D show the light-emitting units covered by different types of protection layers.

DETAILED DESCRIPTION OF THE EMBODIMENTS

The drawings illustrate the embodiments of the application and, together with the description, serve to illustrate the principles of the application. The same name or the same reference number given or appeared in different paragraphs or figures along the specification should have the same or equivalent meanings while it is once defined anywhere of the disclosure. The thickness or the shape of an element in the specification can be expanded or narrowed.

Figure 1A:
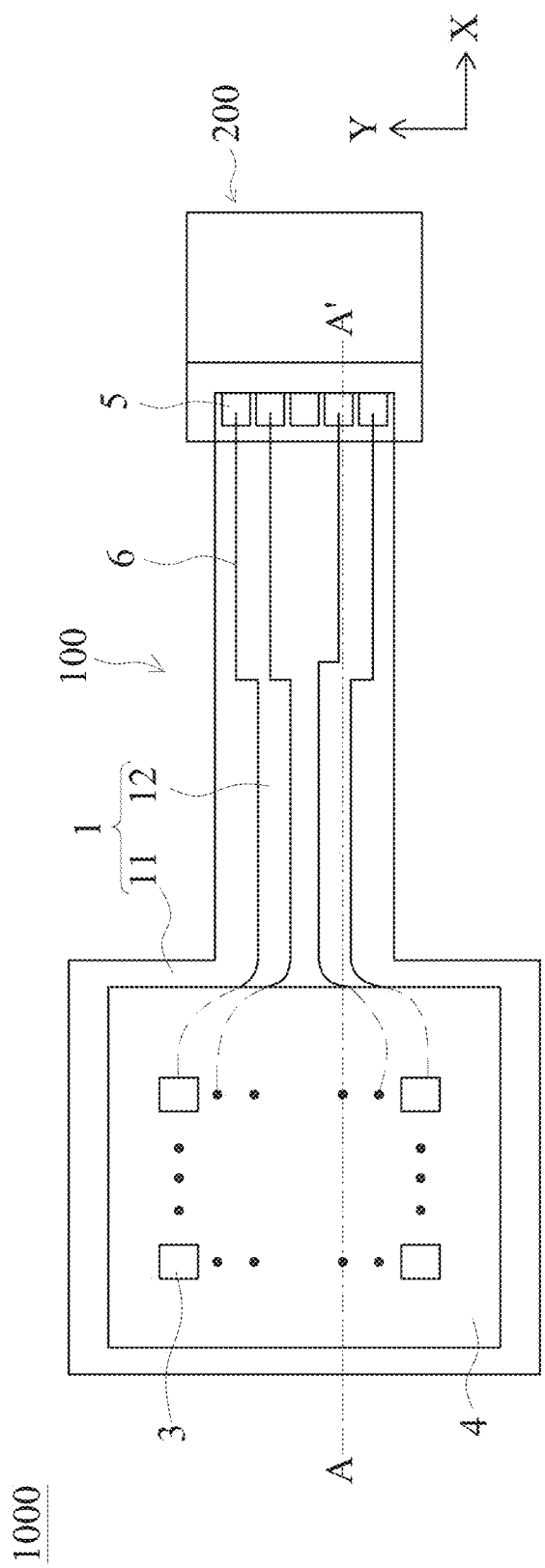
FIG. 1A shows a light-emitting system in accordance with an embodiment of the present disclosure.

FIG. 1A shows a light-emitting system in accordance with an embodiment of the present disclosure. The light-emitting system 1000 includes a light-emitting module 100 and a control module 200. The light-emitting module 100 includes a carrier 1, a plurality of light-emitting units 3, a protection layer 4, and a connecting structure 5. The carrier 1 includes a lighting portion 11 and an extending portion 12. The lighting portion 11 is arranged on one end of the carrier 1. The connecting structure 5 is located on another end of the carrier 1 for connecting to the control module 200. The lighting portion 11 can wrap a portion of human or animal body, such wrist, arm, leg, ankle, for providing a treatment with a stable light intensity and uniform light distribution. The plurality of light-emitting units 3 can emit a non-coherent light to heal treated area(s) of human or animal body which has illness (for example, wound, tumor, or cancer) in accompany of a photosensitive drug placed on the treated area or on a surface of the lighting portion 11. The plurality of light-emitting units 3 is disposed on the lighting portion 11 in an array, interlaced, or a concentric circle arrangement. The plurality of light-emitting units 3 is connected in series, in parallel, or a combination of series and parallel. The plurality of light-emitting units 3 is electrically connected to each other by a plurality of conductive lines on the lighting portion 11 of the carrier 1. The plurality of conductive lines is further electrically connected to the connecting structure 5.

The light-emitting unit 3 has a first conductivity-type semiconductor layer, a second conductivity-type semiconductor layer, and an active stack between the first conductivity-type semiconductor layer and the second conductivity-type semiconductor layer. The first conductivity-type semiconductor layer and the second conductivity-type semiconductor layer each performs as a cladding layer or a confinement layer for respectively providing electrons and holes to be combined in the active layer and emit light accordingly. The first conductivity-type semiconductor layer, the active layer, and the second conductivity-type semiconductor layer can be made of materials including but not limited to group III -V semiconductor material, such as $Al_xIn_yGa_{(1-x-y)}N$ or $Al_xIn_yGa_{(1-x-y)}P$, wherein $0 \leq x, y \leq 1$; $(x+y) \leq 1$. Based on the material composed of the active layer, the light-emitting unit 3 can emit a red light with a peak wavelength roughly between 580 nm and 700 nm, a green light with a peak wavelength roughly between 530 nm and 570 nm, or a blue light with a peak wavelength roughly between 450 nm and 490 nm.

The carrier 1 is flexible and transparent to the light emitted from the light-emitting unit 3. The carrier 1 can be formed of PET, PI (polyimide), HPVDF (hyper-polyvinylidene fluoride), or ETFE (ethylene-tetrafluoro ethylene).

For example, the carrier 1 has a transparency larger than 90% with respect to a light from the light-emitting unit 3. Preferably, the carrier 1 has a transparency between 92%~100% with respect to the light from the light-emitting unit 3, and the carrier 1 is fully cured at a curing temperature between 160° C.~200. Preferably, the carrier 1 has a transparency larger than 90% and a glass transition temperature larger than 160° C. In another embodiment, the extending portion 12 of the carrier 1 is not transparent to the light, but the lighting portion 11 of the carrier 1 is transparent to the light emitted from the light-emitting unit 3.

As shown in FIG. 1A, the light-emitting unit 3 has a dimension which is not larger than 0.15 $mm^2$ in a top view, for example 0.13 $mm^2$, 0.1 $mm^2$, 0.07 $mm^2$, or 0.03 $mm^2$. If the treated area is small, the lighting portion 11 is not necessary to have a big size. Furthermore, the number of the light-emitting unit 3 disposed on the lighting portion 11 can be increased if the dimension of the light-emitting unit 3 is smaller. Hence, the luminous intensity of the lighting portion 11 can be increased and the therapy period can be reduced. In one embodiment, the occupying area of the plurality of light-emitting units 3 is about 20 mm×10 mm. The occupying area of the plurality of light-emitting units 3 is not limited to the number exemplified herein.

The extending portion 12 which is arranged between and connected to the connecting structure 5 and the lighting portion 11 is used to electrically connect the lighting portion 11 and the control module 200. The lighting portion 11 and the extending portion 12 can be bent to meet the contour of the area where they are placed. Furthermore, the extending portion 12 also can be used to further fix the lighting portion 11 on the treated area by wrapping up the treated subject, such as human or animal body. The plurality of conductive lines 6 is disposed on the extending portion 12 and provides a conductive passage for the driving current from the control module 200 to the plurality of light-emitting units 3. The conductive line 6 can be formed by silver paste or copper. The extending portion 12 optionally has no light-emitting unit disposed thereon and does not actively emit light. The extending portion 12 can have an elongated shape in a top view, such as a rectangular shape. The illustrated length of the extending portion 12 is not shown in scale, and can be longer or shorter according to the required distance between the lighting portion 11 and the connecting structure 5. The extending portion 12 has a width less than that of the lighting portion 11 in the y direction. In another embodiment, the width of the extending portion 12 is substantially equal to that of the lighting portion 11 in the y direction. The extending portion 12 and the lighting portion 11 of the carrier 1 can be made of identical or different materials and exhibits a flexible or bendable characteristic. In an embodiment, the extending portion 12 is made of material different from the lighting portion 11, and has a higher flexibility. In addition, the lighting portion 11 and the extending portion 12 can be formed in two separated pieces or in one integrated piece. Two separated pieces can be connected to each other by an adhesive or mechanical means, such as a connector or a clip.

As shown in FIG. 1A, a protection layer 4 covers and protects the plurality of light-emitting units 3 from damage caused from ambient environment. The protection layer 4 can cover the whole or a portion of the lighting portion 11. In other words, the protection layer 4 can cover an area that is substantially equivalent to or smaller than the lighting portion 11. The extending portion 12 is exposed from the protection layer 4.

Figure 1B:
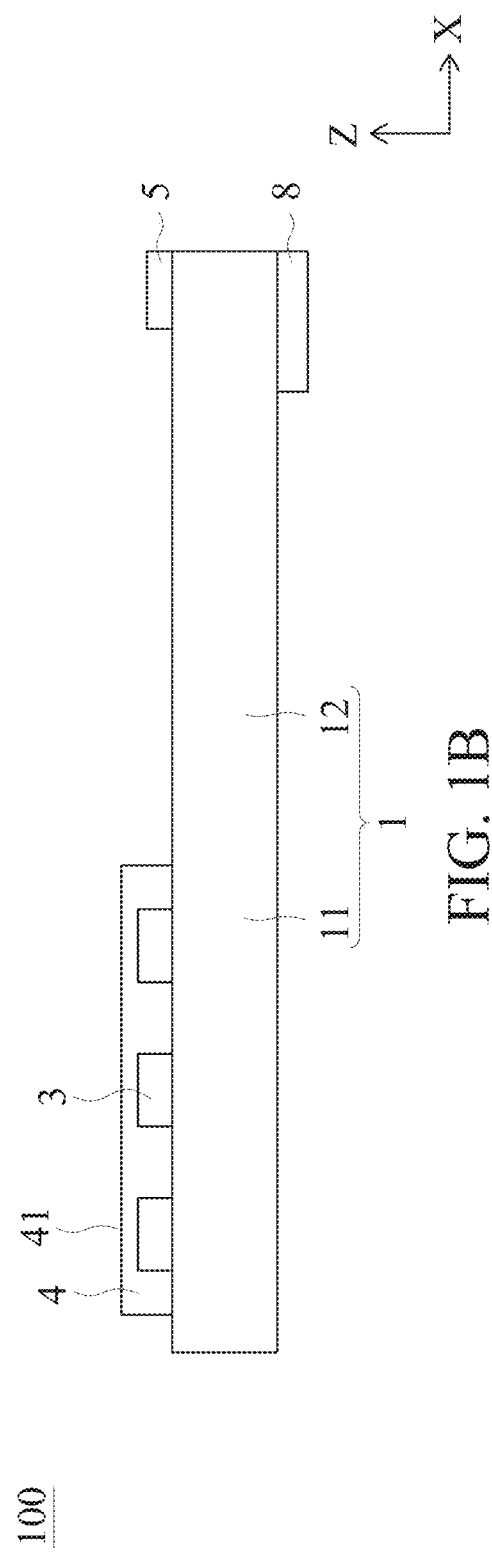
FIG. 1B shows a partial cross-sectional view of the light-emitting module shown in FIG. 1A.

FIG. 1B shows a partial cross-sectional view of the light-emitting module 100 taken along line A-A' in FIG. 1A. The connecting structure 5 is disposed on a side of the extending portion 12 where the light-emitting unit 3 is disposed. In another embodiment, the connecting structure 5 is disposed on another side of the extending portion 12 opposite to the side where the light-emitting unit 3 is disposed. A supporting substrate 8 is located at one end of the extending portion 12 where the connecting structure 5 is located. The supporting substrate 8 is disposed on a side of the extending portion 12 which is opposite to the side where the connecting structure 5 is disposed. The supporting substrate 8 has a thickness of 2~8 mm, for example 4 mm, and is made of the insulating material or conductive material. The supporting substrate 8 is used to strengthen the connecting structure 5 for connection between the extending portion 12 and the control module 200. The top surface and the side surface of the light-emitting unit 3 are covered by the protection layer 4. The lighting portion 11 and the protection layer 4 collectively have a height with a range of 0.2~1 mm, for example 0.2~0.3 mm.

A cream or solution containing a photosensitive drug is applied to a treated area having skin diseases, such as actinic/solar keratoses, Bowen's disease, superficial basal cell carcinoma, squamous cell carcinoma, intraepithelial carcinoma, mycosis fungoides, T-cell lymphoma, acne and seborrhea, eczema, psoriasis, nevus sebaceous, oral cancers (e.g. pre-malignant or dysplastic lesions and squamous cell carcinomas), viral infections such as herpes simplex, molluscum contagiosum, warts (recalcitrant, verruca vulgaris or verruca plantaris), alopecia areata, or hirsutism. The light-emitting module 100 contacts the treated area through the photosensitive drug(s) which has a small thickness. The light-emitting module is very close to, preferably, can directly contact, the photosensitive drug(s). The photosensitive drug(s) can be rapidly released to the treated area for therapy and/or diagnosis after being radiated by the light emitted from the lighting portion 11. The distance between the lighting portion 11 and the treated area is ranged between 0 mm~5 mm. The protection layer 4 is used to prevent the heat produced by the light-emitting unit 3 from burning the treated area of the human or animal body and to prevent the light-emitting units from directly contacting and harming the treated area or the photosensitive drug. The outer surface 41 of the protection layer 4 can contact or approach the treated area (or the photosensitive drug) and has a surface temperature not higher than 50° C. during normal operation, preferably not higher than 40° C. or near the temperature around the treated area of human or animal (for example, 37° C. for human body). The lighting portion 11 can preferably output light about 100 mW/cm2 in a dominant or peak wavelength of 625~635 nm, and/or about 60 mW/cm2 in a dominant or peak wavelength of 405~410 nm.

The protection layer 4 has a transparency lager than 60% in respect to the light from the light-emitting unit 3, and a refractive index of 1.4~1.6. The protection layer can be made of material(s) processing the properties mentioned above, such as polymer or oxide. The polymer includes but not limited to silicone, epoxy, PI, BCB, PFCB, SU8, acrylic resin, PMMA, PET, PC, polyetherimide, or fluorocarbon. The oxide includes but not limited to $Al_2O_3$, SINR, Sub, or SOG.

Figure 1C:
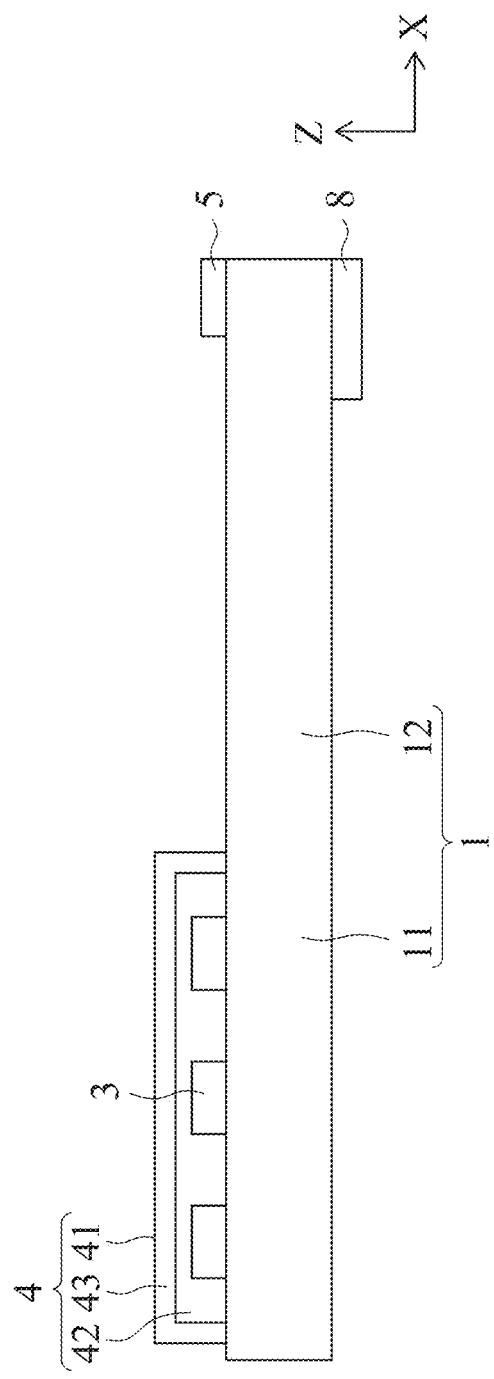
FIG. 1C shows a partial cross-sectional view of the light-emitting module in accordance with another embodiment of the present disclosure.

The protection layer 4 can contact the skin of the human or the animal for therapy. In an embodiment, the material of the protection layer 4 does not contain hazardous substance or mixture shown in GHS (Globally Harmonized System of Classification and Labelling of Chemicals). Preferably, the protection layer 4 is made of biomedical material including biomedical grade elastomer, or biomedical grade silicone rubber which causes less or no side effect, for example, skin sensitisation、skin corrosion/irritation, on the skin of the human or the animal, such as silicone base material. The available product is the SILASTIC® MDX4-4210 Dow-Corning. In another embodiment, the protection layer 4 is a multi-layer structure, as shown in FIG. 1C. The protection layer 4 has at least two layers including inner layer 42 and the outer layer 43. The outer layer 43 is made of biomedical material including biomedical grade elastomer, or biomedical grade silicone rubber for directly contacting the skin of the animal or human. The inner layer 42 can continuously cover the plurality of light-emitting units 3 and is made of one or more transparent encapsulating materials aforementioned above. The inner layer 42 can be thicker than the outer layer 43. In an embodiment, the refractive index of the inner layer 42 is different from that of the outer layer 43. For example, the refractive index of the inner layer 42 is larger than that of the outer layer 43, which improve light extraction.

The light-emitting module 100 can be disposable after one-time use, or reusable device. If the light-emitting module 100 is reusable, outer surface 41 of the protection layer 4 of the lighting portion 11 can be sterilized, cleaned by Alcohol or water after/before using.

The light emitted from the lighting portion 11 can generate a uniform illumination which is an illumination variation of one side of the lighting portion 11 less than ±20%, for example ±10%. The lighting portion 11 can be divided into a plurality of sub-portions (not labeled). The illumination variation of one side is the difference of the luminous intensities measured above the outer surface 41 of the plurality of sub-portions of the lighting portion 11. The luminous intensity can be measured by a luminous intensity measuring instrument, such as light meter. The sub-portion preferably has an area substantially equal to or smaller than the area of the light detecting portion of the luminous intensity measuring instrument.

Figure 1D:
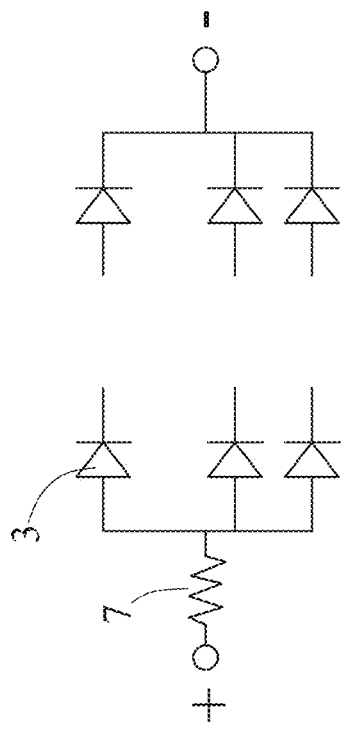
FIG. 1D shows an equivalent circuit of the plurality of light-emitting units in accordance with an embodiment of the present disclosure.

FIG. 1D shows an equivalent circuit of the plurality of light-emitting units 3 in accordance with an embodiment of the present disclosure. The plurality of light-emitting units 3 can be divided into two or more light-emitting groups which are electrically connected in parallel with each other. Each light-emitting group includes multiple light-emitting unit 3 electrically connected in series. An electric component 7, such as a resistor, a capacitor, an inductor, or a rectifier, is located between a driving circuit (not shown) and the plurality of light-emitting units 3 to adjust the current passing through the plurality of light-emitting units 3. In one embodiment, the electric component 7 is located in the control module 200, not located on the lighting portion 11 (or carrier 1). Therefore, the heat coming from the electric component 7 can dissipate through the control module 200. In an embodiment, the plurality of light-emitting units 3 includes six light-emitting units which are divided into three light-emitting groups connected in parallel with each other. Each light-emitting group includes two light-emitting units connected in series. According to the requirement, the light-emitting units is not limited to the number exemplified herein, for example, the number is six or more, or six or less.

In another embodiment, as shown in FIG. 1E, the bottom side of the lighting portion 11, which is opposite to the top side where the light-emitting unit 3 resides, has a reflective layer 9. The reflective layer 9 can reflect the light emitted from the light-emitting unit 3 toward the outer surface 41 of the protection layer 4. During the therapy, the reflective layer 9 not only increases the luminous intensity of the light moving upward the light-emitting module but also prevents light from radiating backward/toward the eyes of human or animal.

FIG. 2 shows an example that the light-emitting module 100 wraps the human's finger 10 to treat the skin disease such as wart. The lighting portion 11 can be bent to meet the contour of the finger 10. The image shown herein, the lighting portion 11 does not have the reflective layer on the bottom surface and the light is emitted toward and backward the finger 10.

Figure 3A:
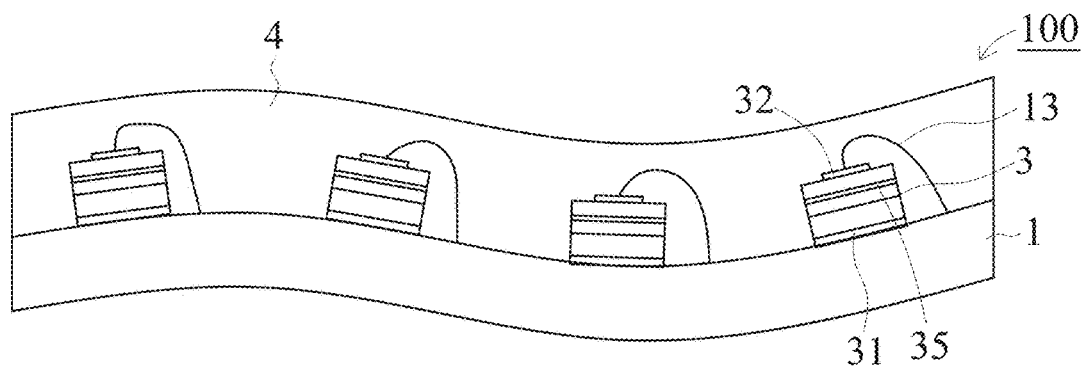
FIGS. 3A~3D show different types of the light-emitting units affixed on carriers in accordance with embodiments of the present disclosure.

FIG. 3A~3D show drawings of the light-emitting modules 100 in a bending situation. The carrier 1 is flexible, and the surface of the carrier 1 can be bent to meet a curve having various curvatures as shown in FIG. 3A~3D. Though the carrier 1 is bent, the light-emitting unit 3 is tightly connected to the carrier 1 by the protection layer 4. The optical properties of the light-emitting module 100 are not perceptive when the carrier 1 is bent. The light-emitting unit 3 can be an LED bare chip, an LED package, or a CSP (Chip Scale Package) LED. FIG. 3A shows the light-emitting unit 3 which is the vertical type LED bare chip. The light-emitting unit 3 has two electrodes 31, 32 which are located on the opposite sides of the light-emitting unit 3. The first electrode 31 is arranged on the bottom side of the light-emitting unit 3 to attach to the carrier 1 by the soldering materials including Sn, Ag, Cu, or Bi. The second electrode 32 is arranged on the top side of the light-emitting unit 3 to connect to the carrier 1 by the bonding wire 13. The bonding wire 13 is covered by the protection layer 4 for preventing damage induced by the bending of the light-emitting module 100.

Figure 3B:
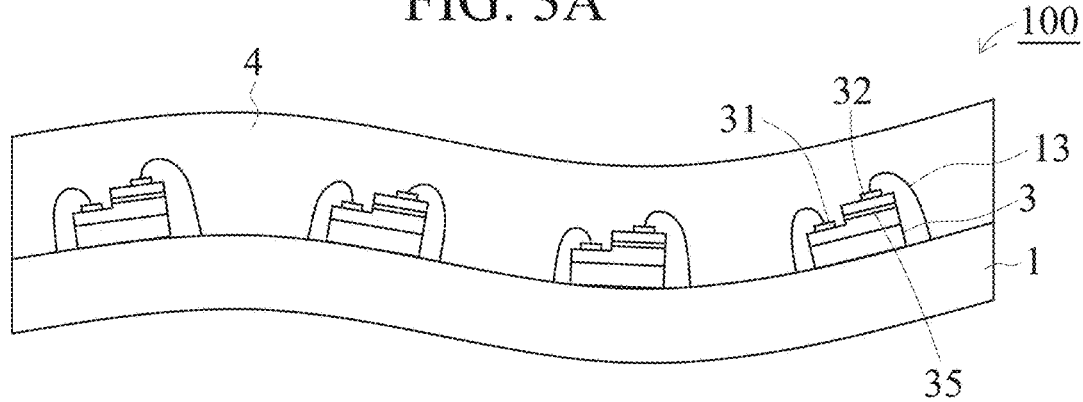
Figure 3C:
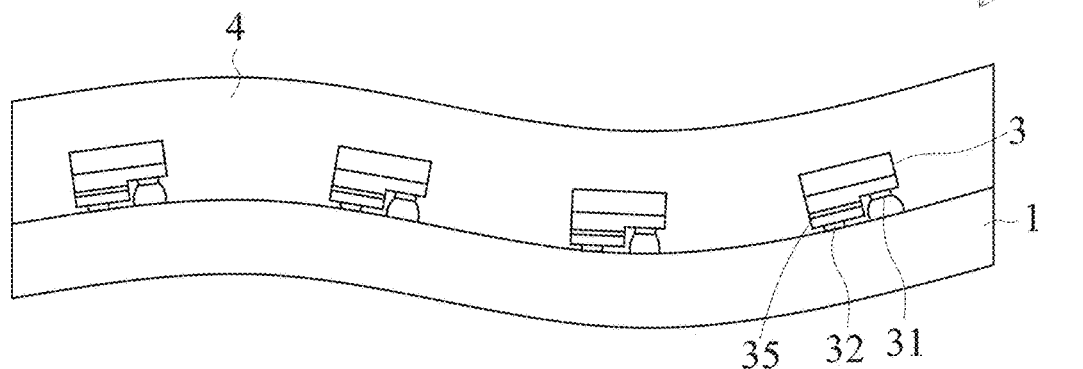
Figure 3D:
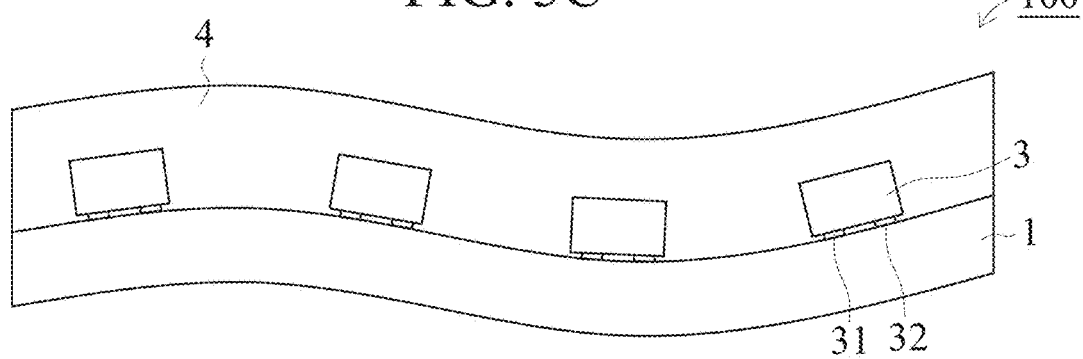

FIG. 3B shows the light-emitting unit 3 is the horizontal type LED bare chip. The light-emitting unit 3 has two electrodes 31, 32 which are located on the same side of the active layer 35 of the light-emitting unit 3. The electrodes 31, 32 are electrically connected to the carrier 1 by the bonding wire 13. The bottom side of the light-emitting unit 3 is affixed on the carrier 1 through the thermally conductive material. The bonding wire 13 is covered by the protection layer 4 for preventing damage induced by the bending of the light-emitting module 100. FIG. 3C shows the light-emitting unit 3 is the horizontal type LED bare chip. The light-emitting unit 3 has two electrodes 31, 32 which are located on the same side of the active layer 35 of the light-emitting unit 3 and flip-bonded on the carrier 1 by the soldering materials including Sn, Ag, Cu, or Bi. The bonding surfaces of the electrodes 31, 32 are not coplanar with each other. FIG. 3D shows the light-emitting unit 3 is the flip-chip type LED bare chip. As shown in FIG. 3D, the light-emitting unit 3 has two electrodes 31, 32 which are located on the bottom side of the light-emitting unit 3 and flip-bond on the carrier 1 by the soldering materials including Sn, Ag, Cu, or Bi. The bonding surfaces of the electrodes 31, 32 are substantially coplanar with each other. In another embodiment, the light-emitting unit 3 shown in FIG. 3D is an LED package. In another embodiment, the light-emitting unit 3 shown in FIG. 3D is a CSP LED.

Figure 4A:
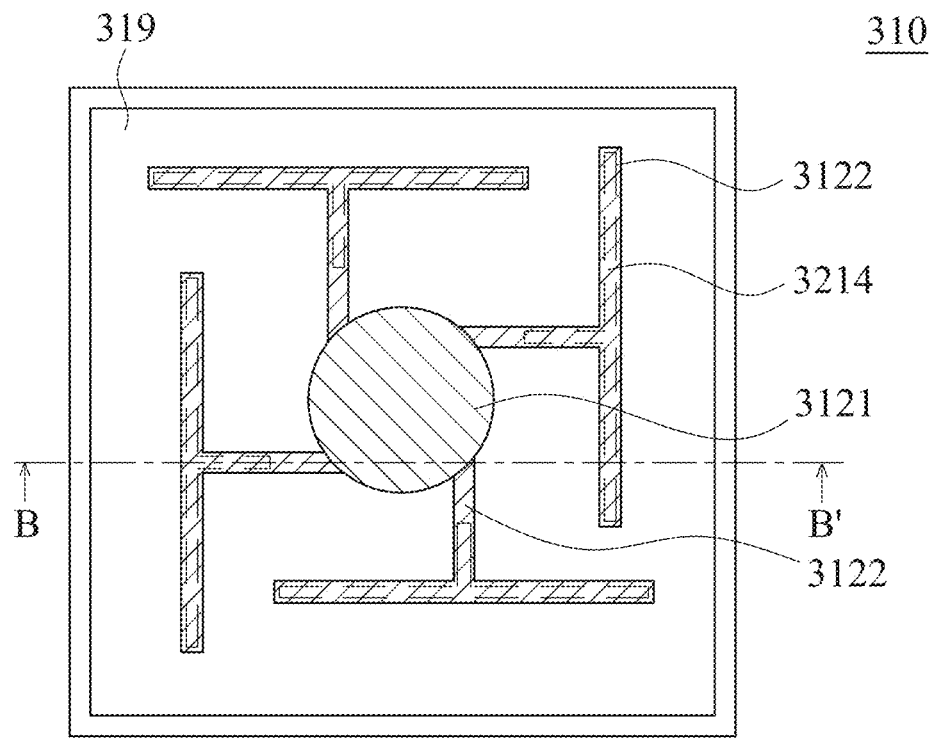
FIG. 4A shows a top view of a light-emitting unit in accordance with an embodiment of the present disclosure.
Figure 4B:
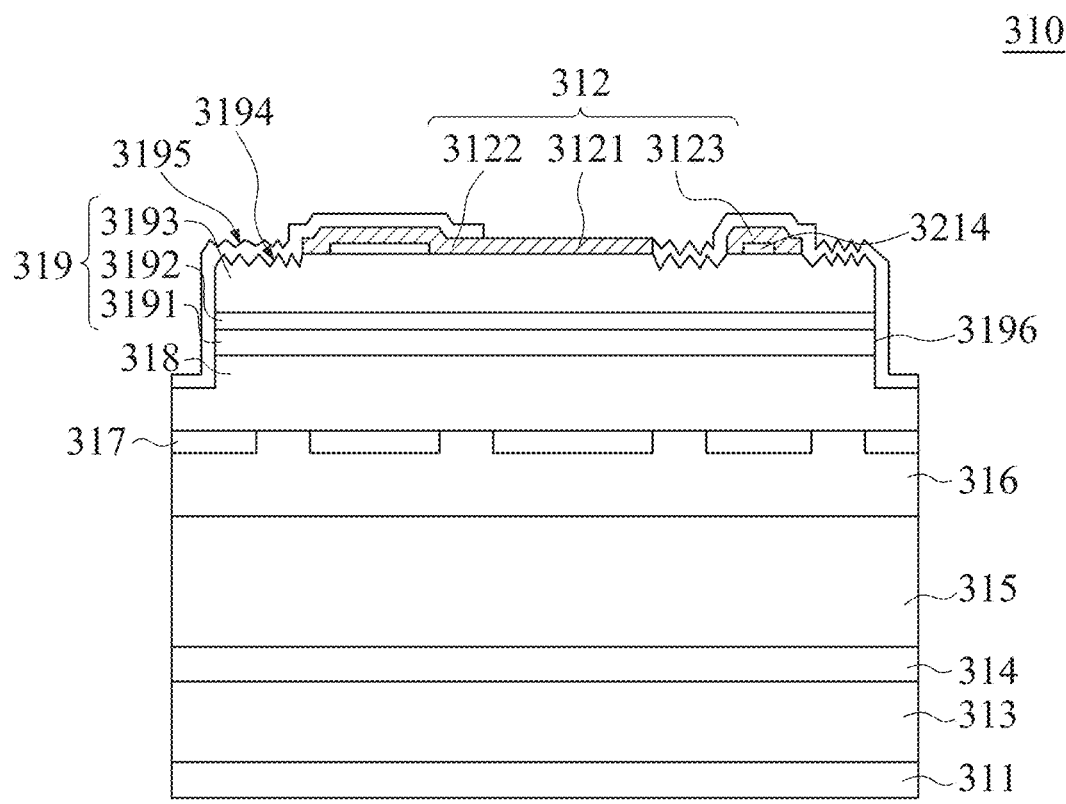
FIG. 4B shows a cross-sectional view of a light-emitting unit shown in FIG. 4A.

FIG. 4A~4B show a light-emitting unit in accordance with an embodiment shown in FIG. 3A. FIG. 4A shows a top view of a light-emitting unit. FIG. 4B shows a cross-sectional view of the light-emitting unit 310 taken along line B-B' in FIG. 4A. As shown in FIG. 4B, light-emitting unit 310 includes a substrate 313, a conductive adhesion layer 314 on the substrate 313, a reflective structure 315 on the conductive adhesion layer 314, a transparent conducting structure 316 on the reflective structure 315, a window layer 318 on the transparent conducting structure 316, a non-oxide insulation layer 317 between the transparent conducting structure 316 and the window layer 318, a light-emitting stack 319 on the window layer 318, an electrical contact layer 3214 on the light-emitting stack 319, a first electrode 312 on the light-emitting stack 319, and a second electrode 311 below the substrate 313.

The light-emitting stack 319 includes the first conductivity-type semiconductor layer 3191, the second conductivity-type semiconductor layer 3193, and the active stack 3192 between the first conductivity-type semiconductor layer 3191 and the second conductivity-type semiconductor layer 3193. The related descriptions about the first conductivity-type semiconductor layer 3191, the second conductivity-type semiconductor layer 3193, and the active stack can refer to aforementioned paragraph related to FIG. 1A. An upper light-exiting surface 3194 of the second conductivity-type semiconductor layer 3193 can be a rough surface for reducing total internal reflection, so as to increase luminous efficiency of the light-emitting unit 310. The window layer 318 can be beneficial to light extraction and increase the luminous efficiency. The polarity of the window layer 318 can be the same as the first conductivity-type semiconductor layer 3191.

The first electrode 312 and/or the second electrode 311 are used for die-bonding to an external device, such as a package sub-mount or a printed circuit board through a wire or a solder bump, an example shown in FIG. 3A, and made of a transparent conducting material or a metallic material. The transparent conducting material includes, but not limited to indium tin oxide (ITO), indium oxide (InO), tin oxide (SnO), cadmium tin oxide (CTO), antimony tin oxide (ATO), aluminum zinc oxide (AZO), zinc tin oxide (ZTO), gallium zinc oxide (GZO), indium tungsten oxide (IWO), zinc oxide (ZnO), aluminum gallium arsenide (AlGaAs), gallium nitride (GaN), gallium phosphide (GaP), gallium arsenide (GaAs), gallium arsenide phosphide (GaAsP), indium zinc oxide (IZO), and diamond like carbon (DLC). The metallic material includes, but not limited to aluminum (Al), chromium (Cr), copper (Cu), tin (Sn), gold (Au), nickel (Ni), titanium (Ti), platinum (Pt), lead (Pb), zinc (Zn), cadmium (Cd), antimony (Sb), cobalt (Co), and an alloy including the abovementioned. The first electrode 312 electrically connects the second conductivity-type semiconductor layer 3193 and includes a current input portion 3121 and an extension portion 3122. As shown in FIG. 4A, the current input portion 3121 is substantially located on a center of the second conductivity-type semiconductor layer 3193, and the extension portion 3122 extends from the current input portion 3121 to a boundary of the light-emitting unit 310 for improving current diffusion. As shown in FIG. 4B, the extension portion 3122 includes a protrusive portion 3123 on the electrical contact layer 3214 for increasing ohmic contact area with the electrical contact layer 3214, wherein the protrusive portion 3123 is higher than the current input portion 3121. The second electrode 311 is located below the substrate 313 and electrically connects the first conductivity-type semiconductor layer 3191.

The electrical contact layer 3214 is located between and ohmic contacts the extension portion 3122 and the light-emitting stack 319. The electrical contact layer 3214 can be made of a semiconductor material including at least one element, like gallium (Ga), aluminum (Al), indium (In), phosphorus (P), nitrogen (N), zinc (Zn), cadmium (Cd), or selenium (Se). The electrical contact layer 3214 and the second conductivity-type semiconductor layer 3193 can have the same polarity.

The window layer 318 is transparent to light emitted from the active stack 3192. Additionally, the window layer 318 can be made of a transparent conducting material including but not limited to indium tin oxide (ITO), indium oxide (InO), tin oxide (SnO), cadmium tin oxide (CTO), antimony tin oxide (ATO), aluminum zinc oxide (AZO), zinc tin oxide (ZTO), gallium zinc oxide (GZO), indium tungsten oxide (IWO), zinc oxide (ZnO), magnesium oxide (MgO), aluminum gallium arsenide (AlGaAs), gallium nitride (GaN), gallium phosphide (GaP), and indium zinc oxide (IZO).

As shown in FIG. 4B, the maximum width of the light-emitting stack 319 is less than that of the window layer 318. The window layer 318 has an upper portion contacting the light-emitting stack 319 and having a width equal to the light-emitting stack 319, and has a lower portion contacting the non-oxide insulation layer 317 and having a width larger than the light-emitting stack 319. In other words, a portion of the top surface of the window layer 318 is not covered by the light-emitting stack 319. The outmost side surface 3196 of the light-emitting stack 319 is not coplanar with the outmost side surface 3181 of the window layer 318. As shown is FIG. 4A, the area of the light-emitting stack 319 is smaller than the area of the substrate 313 in the top view. The light-emitting stack 319 is located about the center of the light-emitting unit 310.

The passivation layer 3195 is formed along the contour of the side surface of the window layer 318 and the light-emitting stack 319, and the top surface of the upper light-exiting surface 3194, and the extension portion 3122 of the first electrode 312. The passivation layer 3195 exposes the current input portion 3121 of the first electrode 312 for connecting to an external device. The top surface above the light-emitting stack 319 of the passivation layer 3195 is uneven and has a contour similar to the topography of the upper light-exiting surface 3194 and the protrusive portion 3123 of the first electrode 312. The passivation layer 3195 can be made of the transparent insulation material such as $SiO_x$, silicon nitride ($SiN_x$), SiON, or $AlO_x$.

The transparent conducting structure 316 is transparent to light emitted from the light-emitting stack 319, and can improve the ohmic contact between the window layer 318 and the reflective structure 315. Additionally, the transparent conducting structure 316 and the reflective structure 315 can be formed an omni-directional reflector (ODR) which is made of a transparent material including but not limited to indium tin oxide (ITO), indium oxide (InO), tin oxide (SnO), cadmium tin oxide (CTO), antimony tin oxide (ATO), aluminum zinc oxide (AZO), zinc tin oxide (ZTO), gallium zinc oxide (GZO), indium tungsten oxide (IWO), zinc oxide (ZnO), gallium phosphide (GaP), indium cerium oxide (ICO), indium titanium oxide (ITiO), indium zinc oxide (IZO), indium gallium oxide (IGO), gallium aluminum zinc oxide (GAZO), and a combination thereof.

The transmittance of the non-oxide insulation layer 317 to the light emitted from the light-emitting stack 319 is greater than 90%. A material of the non-oxide insulation layer 317 can be a non-oxide insulation material, for example, benzocyclobutene (BCB), cyclic olefin copolymers (COC), fluorocarbon polymer, silicon nitride ($SiN_x$). In another embodiment, a material of the non-oxide insulation layer 317 can include a halide, a compound of group IIA, or a compound of group VIIA, for example, calcium difluoride ($CaF_2$), carbon tetrafluoride ($CF_4$) or magnesium difluoride ($MgF_2$). The non-oxide insulation layer 317 has a plurality of separated portions embedded in the transparent conducting structure 316. The non-oxide insulation layer 317 has a plurality separated top surfaces which contact the window layer 318 and are coplanar with the top surface of the transparent conducting structure 316. The non-oxide insulation layer 317 can be formed as a pattern, for example, a pattern right under the electrical contact layer 3214 and/or the current input portion 3121 for diffusing the current. In another embodiment, the non-oxide insulation layer 317 can have random pattern or is not located right under the electrical contact layer 3214 and/or the current input portion 3121. The non-oxide insulation layer 317 has a thickness less than a half of a thickness of the transparent conducting structure 316. At least one bottom surface of the non-oxide insulation layer 317 is covered by the transparent conducting structure 316 for strongly joining to the reflective structure 315. In another embodiment, the non-oxide insulation layer 317 penetrates through the transparent conducting structure 316 and directly joins the reflective structure 315.

The reflective structure 315 can reflect light emitted from the light-emitting stack 319, and the reflective structure 315 can be made of metallic material including, but not limited to copper (Cu), aluminum (Al), tin (Sn), gold (Au), silver (Ag), lead (Pb), titanium (Ti), nickel (Ni), platinum (Pt), tungsten (W) and an alloy made of the above mentioned.

The substrate 313 can support the light-emitting stack 319 and other layers or structures, and be made of a transparent material or a conductive material. For example, the transparent material can include, but not limited to sapphire, diamond, glass, epoxy, quartz, acryl, $Al_2O_3$, zinc oxide (ZnO), and aluminum nitride (AlN); the conductive material can include, but not limited to copper (Cu), aluminum (Al), molybdenum (Mo), tin (Sn), zinc (Zn), cadmium (Cd), nickel (Ni), cobalt (Co), diamond like carbon (DLC), graphite, carbon fiber, metal matrix composite (MMC), ceramic matrix composite (CMC), silicon (Si), zinc selenide (ZnSe), gallium arsenide (GaAs), silicon carbide (SiC), gallium phosphide (GaP), gallium arsenide phosphide (GaAsP), indium phosphide (InP), $LiGaO_2$, and $LiAlO_2$. The conductive adhesion layer 314 connects the substrate 313 and the reflective structure 315. The conductive adhesion layer 314 can be made of transparent conducting material or metallic material. The transparent conducting material comprises indium tin oxide (ITO), indium oxide (InO), tin oxide (SnO), cadmium tin oxide (CTO), antimony tin oxide (ATO), aluminum zinc oxide (AZO), zinc tin oxide (ZTO), gallium zinc oxide (GZO), zinc oxide (ZnO), gallium phosphide (GaP), indium cerium oxide (ICO), indium tungsten oxide (IWO), indium titanium oxide (ITiO), indium zinc oxide (IZO), indium gallium oxide (IGO), gallium aluminum zinc oxide (GAZO), and a combination thereof. The metallic material comprises copper (Cu), aluminum (Al), tin (Sn), gold (Au), silver (Ag), lead (Pb), titanium (Ti), nickel (Ni), platinum (Pt), tungsten (W), and an alloy made of the above mentioned.

Figure 5A:
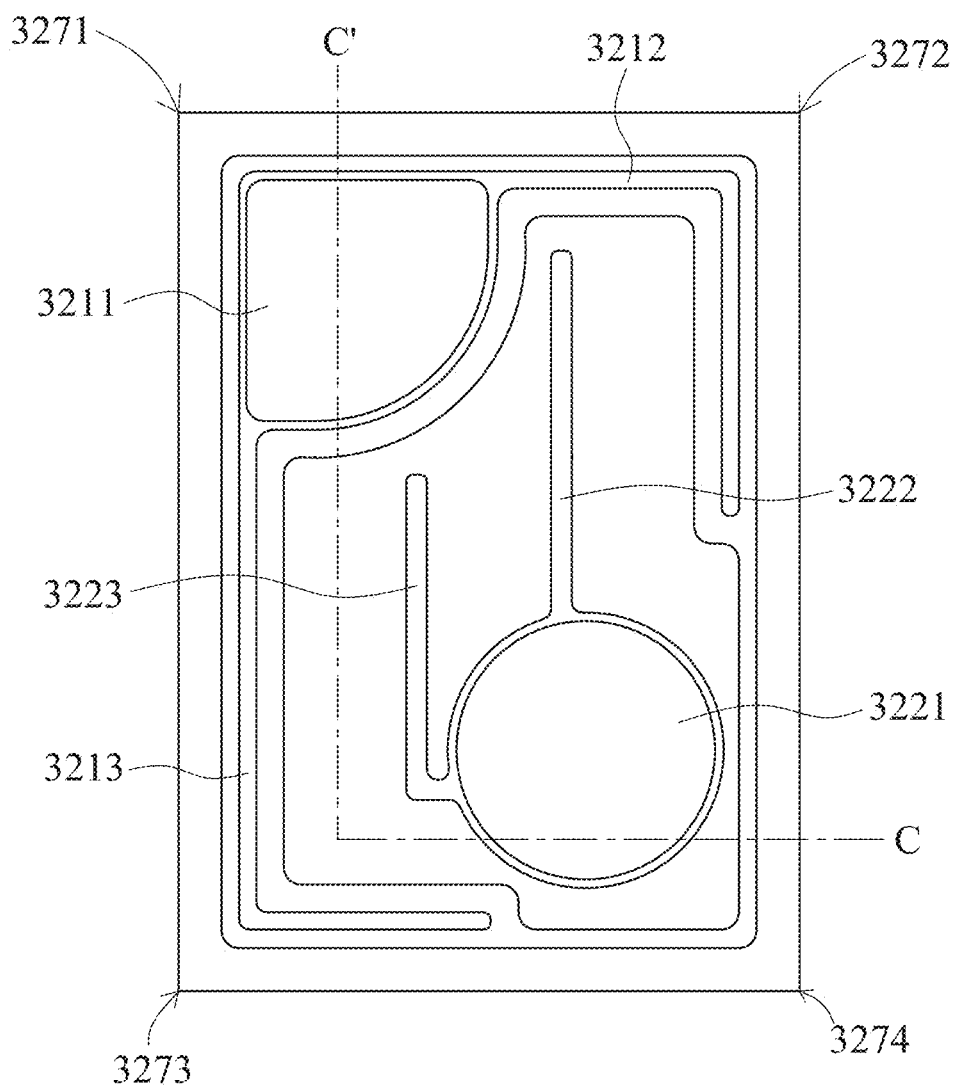
FIG. 5A shows a top view of a light-emitting unit in accordance with another embodiment of the present disclosure.
Figure 5B:
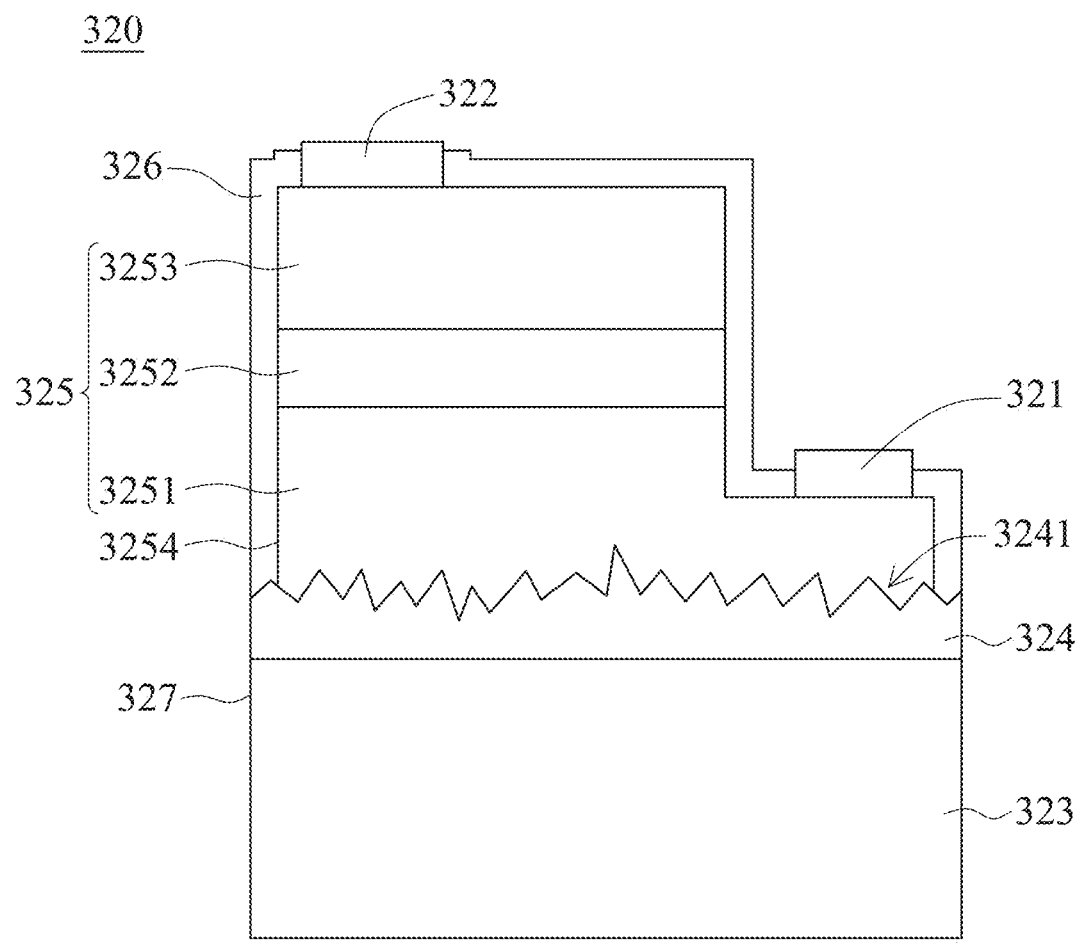
FIG. 5B shows a cross-sectional view of a light-emitting unit shown in FIG. 5A.

FIG. 5A~5B show a light-emitting unit in accordance with an embodiment shown in FIG. 3B. FIG. 5A shows a top view of a light-emitting unit 320. FIG. 5B shows a cross-sectional view of the light-emitting unit 320 taken along line C-C' in FIG. 5A. As shown in FIG. 5B, light-emitting unit 320 includes a substrate 323, a conductive adhesion layer 324 on the substrate 323, a light-emitting stack 325 on conductive adhesion layer 324, and a first electrode 321 and a second electrode 322 on the same side opposite to the substrate 323 of the light-emitting stack 325. The light-emitting stack 325 includes the first conductivity-type semiconductor layer 3251, the second conductivity-type semiconductor layer 3253, and the active stack 3252 between the first conductivity-type semiconductor layer 3251 and the second conductivity-type semiconductor layer 3253. The related descriptions about the light-emitting stack 325 can refer to the aforementioned descriptions related to FIG. 4A~4B. The substrate 323 is made of the transparent material and can refer to the aforementioned descriptions related to FIG. 4A~4B.

The conductive adhesion layer 324 is formed on the substrate 323, and the conductive adhesion layer 324 can be made of polyimide, benzocyclobutene (BCB), perfluorocyclobutane (PFCB) or indium tin oxide. The conductive adhesion layer 324 has a diffusing surface 3241 which is rough surface. In other words, the first conductivity-type semiconductor layer 3251 has a diffusing surface 3241 which contacts the conductive adhesion layer 324. The diffusing surface 3241 is formed during the epitaxial process, or by etching a part of the first conductivity-type semiconductor layer 3251 through wet etching or dry etching, such as inductive coupling plasma (ICP), during the epitaxial process. Hence, the light-emitting stack 325 having a rough surface attached to the substrate 323 by the conductive adhesion layer 324. In another embodiment, the diffusing surface 3241 of the first conductivity-type semiconductor layer 3251 may comprise a plurality of micro protrusions and attaches to the substrate 323 through the conductive adhesion layer 324. The shape of the micro protrusions can be a semi-sphere, a pyramid or a pyramid polygon. Because of the micro protrusions, the diffusing surface 3241 is roughened, and the light extraction efficiency is enhanced.

The first electrode 321 and/or the second electrode 322 are used for die-bonding to an external device, such as a package sub-mount or a printed circuit board through a wire or a solder bump, an example shown in FIG. 3B. The material of the electrodes can refer to the aforementioned descriptions related to FIG. 4A~4B. The first electrode 321 electrically connects the first conductivity-type semiconductor layer 3251 and has a topmost surface lower than the topmost surface of the second conductivity-type semiconductor layer 3253. As shown in FIG. 5A, the first electrode 321 includes a current input portion 3211 and at least one extension portions 3212, 3213. The current input portion 3211 is at a first corner 3271 of the light-emitting unit 320, and the extension portions 3212, 3213 extends from the current input portion 3211 and along the boundary of the light-emitting unit 320 for improving current diffusion. The extension portion 3212 has a right angle at a second corner 3272 adjacent to the first corner 3271. The extension portion 3213 has a right angle at a third corner 3273 adjacent to the first corner 3271 and diagonal to the second corner 3272. The second electrode 322 electrically connects the second conductivity-type semiconductor layer 3253 and has a topmost surface higher than the topmost surface of the second conductivity-type semiconductor layer 3253. The second electrode 322 includes a current input portion 3221 and at least one extension portions 3222, 3223. As shown in FIG. 5A, the current input portion 3221 is at a fourth corner 3274 diagonal to the first corner 3271 of the light-emitting unit 320 and has a different shape from the current input portion 3211 of the first electrode 321. The extension portions 3222, 3223 are also used for improving current diffusion and extend from the current input portion 3221 toward a side between the first corner 3271 and the second corner 3272. The extension portions 3222, 3223 are substantially parallel with a side between the first corner 3271 and the third corner 3273. The number of the extension portions is exemplified herein and not limited to two.

As shown in FIG. 5B, in the cross-sectional view, the maximum width of the light-emitting stack 325 is less than that of conductive adhesion layer 324 and the substrate 323. In other words, a portion of the top surface of the conductive adhesion layer 324 is not covered by the light-emitting stack 325. The outmost side surface 3254 of the light-emitting stack 325 is not coplanar with the outmost side surface 327 of the conductive adhesion layer 324 or/and the substrate 323. As shown is FIG. 5A, the area of the light-emitting stack 325 is smaller than the area of the substrate 323 in the top view. The light-emitting stack 325 is located at the center of the light-emitting unit 320.

The passivation layer 326 is formed along the contour of the outmost side surface 3254 of the light-emitting stack 325, the top surface of the light-emitting stack 325, the extension portions 3212, 3213 of the first electrode 321, and the extension portions 3222, 3223 of the second electrode 322. The passivation layer 326 exposes the current input portion 3211 of the first electrode 321 and the current input portion 3221 of the second electrode 322 for connecting to an external device. The top surface above the light-emitting stack 325 of the passivation layer 3195 is uneven due to the extension portions. In another embodiment, the passivation layer 326 exposes the extension portions 3212, 3213, 3222, 3223. The material of the passivation layer 326 can refer to aforementioned descriptions related to FIG. 4A~4B.

Figure 6A:
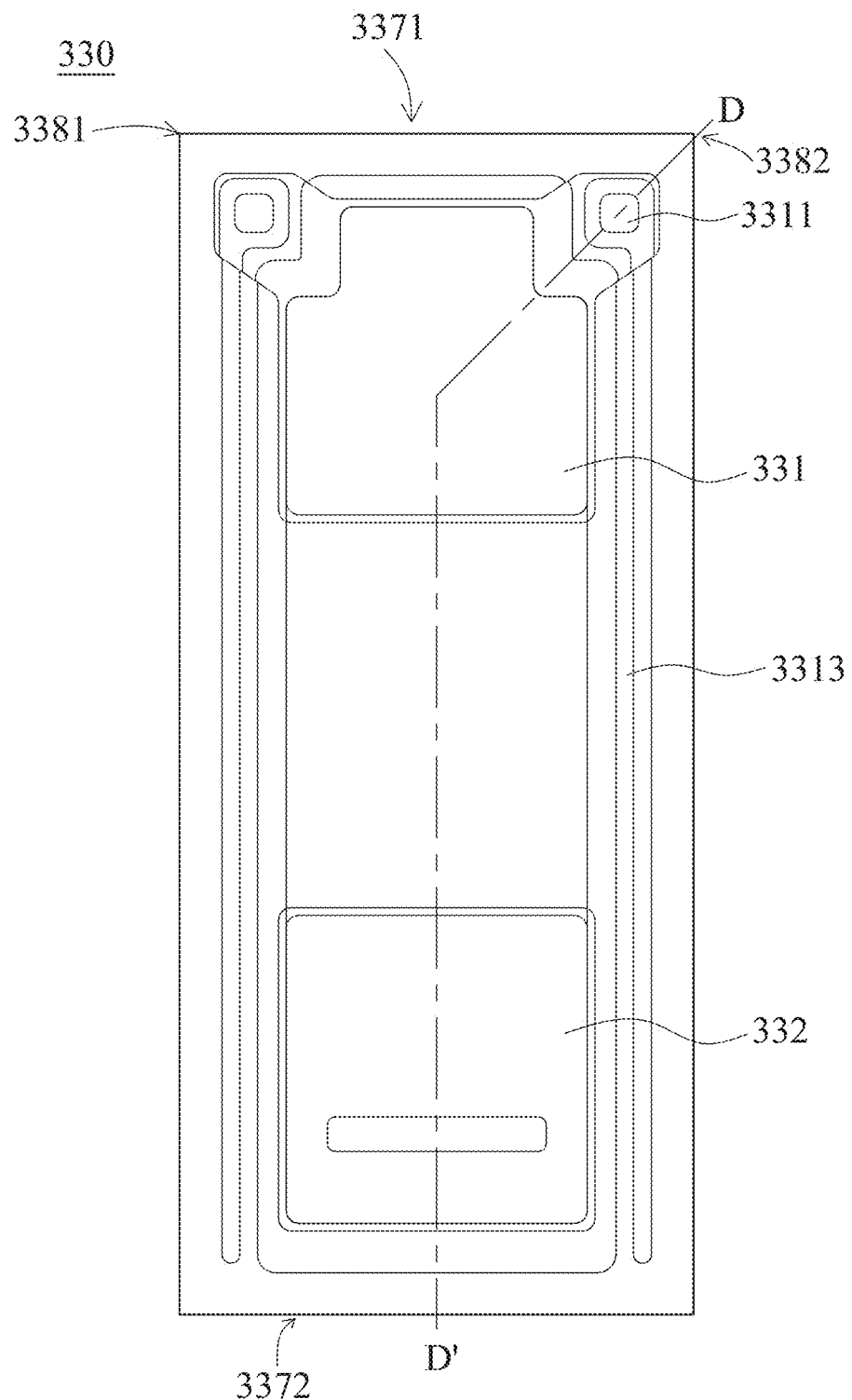
FIG. 6A shows a top view of a light-emitting unit in accordance with a further embodiment of the present disclosure.
Figure 6B:
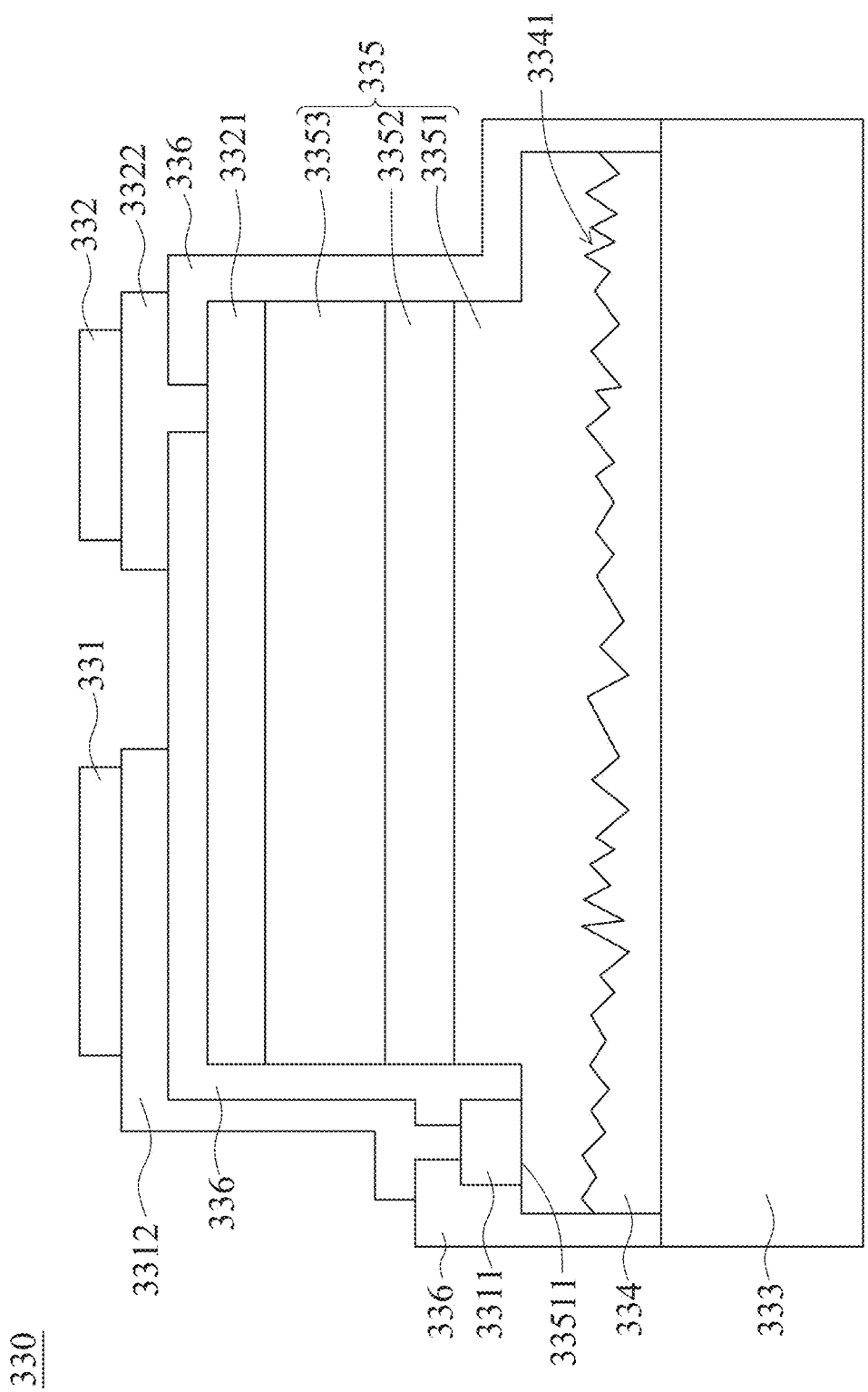
FIG. 6B shows a cross-sectional view of a light-emitting unit shown in FIG. 6A.

FIG. 6A~6B show a light-emitting unit in accordance with an embodiment shown in FIG. 3D. FIG. 6A shows a top view of a light-emitting unit 330. FIG. 6B shows a cross-sectional view of the light-emitting unit 330 taken along line D-D' in FIG. 6A. As shown in FIG. 6B, light-emitting unit 330 includes a substrate 333, a conductive adhesion layer 334 on the substrate 333, a light-emitting stack 335 on conductive adhesion layer 334, and a first electrode 331 and a second electrode 332 on the same side of the light-emitting stack 335. The light-emitting stack 335 includes the first conductivity-type semiconductor layer 3351, the second conductivity-type semiconductor layer 3353 and the active stack 3352 between the first conductivity-type semiconductor layer 3351 and the second conductivity-type semiconductor layer 3353. The related descriptions about the light-emitting stack 335 can refer to the aforementioned descriptions related to FIG. 4A~4B. The substrate 333 is made of the transparent material and can refer to the aforementioned descriptions related to FIG. 4A~4B. The conductive adhesion layer 334 has a width less than the substrate 333 and a diffusing surface 3341 which is rough and contacts the light-emitting stack 335. The details of the conductive adhesion layer 334 can refer to aforementioned descriptions related to FIG. 5A~5B. As shown in FIG. 6B, the light-emitting stack 335 has two portions with different widths which are an upper portion and a lower portion. The upper portion includes the second conductivity-type semiconductor layer 3353, the active stack 3352, and the upper portion of the first conductivity-type semiconductor layer 3351. The lower portion of the light-emitting stack 335 includes the lower portion of the first conductivity-type semiconductor layer 3351. The upper portion of the light-emitting stack 335 has a width less than the lower portion of the light-emitting stack 335 in the cross-sectional view. Hence, an exposed top surface 33511 of the first conductivity-type semiconductor layer 3351 is not covered by the second conductivity-type semiconductor layer 3353 and the active stack 3352. The lower portion of the first conductivity-type semiconductor layer 3351 has a width substantially equal to the conductive adhesion layer 334.

The first electrical contact layer 3311 is disposed on the exposed top surface 33511 of the first conductivity-type semiconductor layer 3351 and electrically connects the first conductivity-type semiconductor layer 3351. The second electrical contact layer 3321 is disposed on the top surface of the second conductivity-type semiconductor layer 3353 and electrically connects the second conductivity-type semiconductor layer 3353. The topmost surface of the first electrical contact layer 3311 is lower than that of the second electrical contact layer 3321. The passivation layer 336 is formed along the contour of the side surface of the conductive adhesion layer 334, and the light-emitting stack 335, the top surface of the first electrical contact layer 3311, and the top surface of the second electrical contact layer 3321. The passivation layer 336 can expose a portion of the top surface of the first electrical contact layer 3311 and the second electrical contact layer 3321. The material of the passivation layer can refer to the aforementioned descriptions related to FIG. 4A~4B.

The first conductive connection layer 3312 extends from the exposed first electrical contact layer 3311 and is formed along the contour of the side surface and the top surface of the passivation layer 336. The second conductive connection layer 3322 extends from the exposed second electrical contact layer 3321 and covers the top surface of the passivation layer 336. The first conductive connection layer 3312 is separated from the second conductive connection layer 3322 by a distance larger than zero, i.e. a portion of the top surface of the passivation layer 336 is not covered by the first conductive connection layer 3312 and the second conductive connection layer 3322. The topmost surfaces of the first conductive connection layer 3312 and the second conductive connection layer 3322 are substantially coplanar with each other. The first electrode 331 is formed on the first conductive connection layer 3312, and the second electrode 332 is formed on the first conductive connection layer 3312. The first electrode 331 is separated from the second electrode 332 by a distance larger than zero. The topmost surfaces of the first electrode 331 and the second electrode 332 are substantially coplanar with each other. As shown in FIG. 6B, above the second conductivity-type semiconductor layer 3353, the shortest distance between the first electrode 331 and the second electrode 332 is larger than the shortest distance between the first conductive connection layer 3312 and the second conductive connection layer 3322. The electrical contact layers 3311, 3321, the conductive connection layers 3312, 3322, and/or the electrodes 331, 332 can be made of the metallic material which can refer to the aforementioned descriptions related to the electrode in FIG. 4A~4B. The outmost side surfaces of the electrode 331, the conductive connection layer 3312, and the passivation layer 336 are not coplanar with each other. The outmost side surfaces of the electrode 332, the conductive connection layer 3322, and the passivation layer 336 are not coplanar with each other.

As shown in FIG. 6A, the first electrode 331 is located close to the first terminal 3371 and the second electrode 332 is located close to the second terminal 3372 opposite to the first terminal 3371 of the light-emitting unit 330. Two electrical contact layers 3311 which are physically separated from each other are located close to the first corner 3381 and the second corner 3382 which are located close to the first terminal 3371. The extension portion 3313 originates from the electrical contact layer 3311 and extends along the elongated side of the light-emitting unit 330. The extension portion 3313 is covered by the passivation layer 336 and used for improving current diffusion.

Figure 7A:
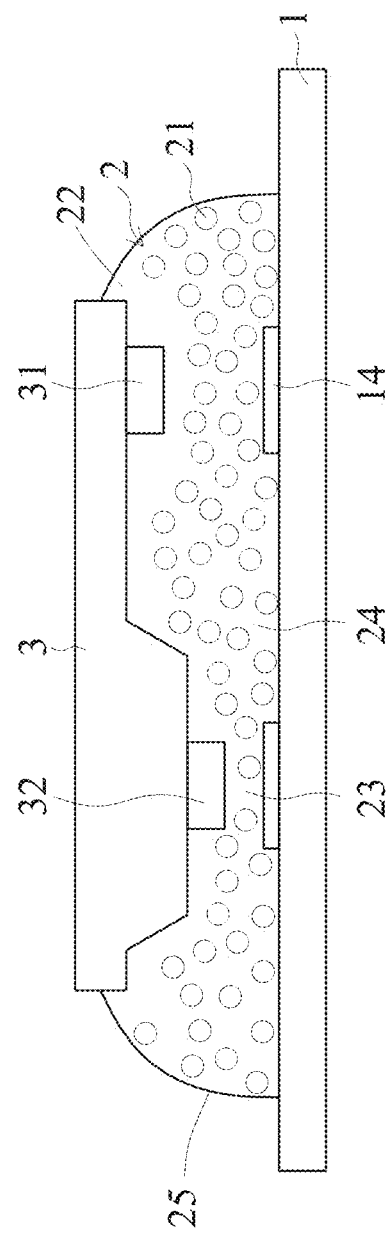
FIGS. 7A~7B show a light-emitting unit affixed on the carrier by a paste in accordance with an embodiment of the present disclosure.
Figure 7B:
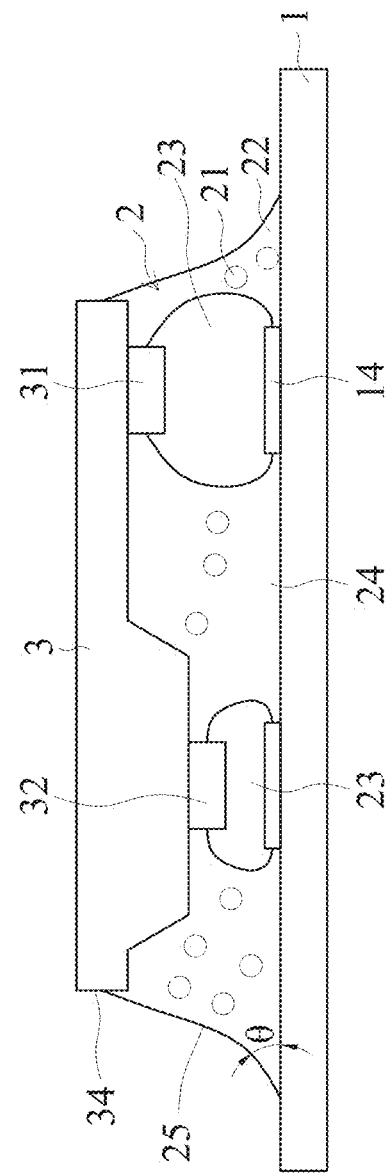

FIG. 7A~7B show a bonding process of an LED bare chip, such as light-emitting unit 320 shown in FIG. 5A~5B which is flip-bonded on the carrier 1 by the paste 2. The paste 2 includes the insulating material 22 and the plurality of conductive particles 21 dispersed in the insulating material 22. The light-emitting unit 3 is placed on the carrier 1 and a paste 2 distributes between the light-emitting unit 3 and the carrier 1. The carrier 1 has a plurality of the conductive pads 14 which is configured to electrically connect to the electrodes 31, 32 of the light-emitting unit 3. The method of bonding the light-emitting unit 3 comprises a heating step. FIG. 7A shows the bonding process before the heating step. FIG. 7B shows the bonding process after the heating step. A distance between the light-emitting unit 3 and the carrier 1 in a normal direction respect to the carrier 1 is substantially the same before and after the heating step. The region covered by the paste 2 includes a conductive portion 23 and a non-conductive portion 24. The conductive portion 23 is located between the electrode 31 and the conductive pad 14, and between the electrode 32 and the conductive pad 14. As shown in FIG. 7A, the bonding process before the heating step, the average weight percentage concentration (or average density) of the conductive particles 21 in the conductive portion 23 is similar to the average weight percentage concentration in the non-conductive portion 24. As shown in the FIG. 7B, the bonding process after the heating step, the most of the conductive particles 21 are gathered in the conductive portion 23. The average weight percentage concentration (or average density) of the conductive particles 21 in the conductive portion 23 is larger than in the non-conductive portion 24. In an embodiment, the average weight percentage concentration (or average density) of the conductive particles 21 in the conductive portion 23 is higher than 75%, or the conductive portion 23 is preferably devoid of the insulating material 22. The average weight percentage concentration (or average density) of the conductive particles 21 in the non-conductive portion 24 is lower than 40%, but not equal to zero. That is, the non-conductive portion 24 comprises small amount of the conductive particles 21. For example, the content of the conductive particles 21 in the non-conductive portion 24 is between 0.1% and 40%, and preferably between 2% and 10%. The average weight percentage concentration (or average density) of the insulating material 22 in the non-conductive portion 24 is higher than 60%, and preferably between 60% and 99.9%, and more preferably between 90% and 98%. In one embodiment, the non-conductive portion 24 comprises 10% to 40% of the conductive particles 21 and 60% to 90% of the insulating material 22, and preferably, the non-conductive portion 24 comprises 20% to 30% of the conductive particles 21 and 70% to 80% of the insulating material 22.

The paste 2 can be divided into several sub portions (for example, 3~10 sub portions). The average weight percentage concentration (or average density) is defined as an average value of all of the weight percentage concentration (or density) of sub portions. The dimension of the sub portion is adjusted based on the size of the testing sample or the measuring method. For example, the sub portion has a 2-dimensional shape in a cross-sectional view or 3-dimensional shape. The 2-dimensional shape can be octagon, hexagon, rectangle, triangle, round, oval, or combinations thereof. The 3-dimensional shape can be a cylinder, cube, cuboid, or sphere. The density of the conductive particles 21 can be calculated by the particle quantity or the area of all conductive particles 21 within a predetermined area (for example 20×20 µm$^2$) of the sub portion of the paste 2.

The conductive particles 21 can be made of metallic material with a melting point lower than 300° C. The metallic material can be an element, a compound, or an alloy, such as bismuth (Bi), tin (Sn), silver (Ag) or indium (In), or the alloy such as Sn—Bi—Ag alloy. When the conductive particles 21 are alloy, the melting point of the conductive particles 21 means the eutectic point of the alloy. The insulating material 22 can be a thermosetting polymer, such as epoxy, silicone, poly (methyl 2-methylpropenoate) and episulfide. The insulating material 22 can be cured at a curing temperature. The melting point of the conductive particles 21 is lower than the curing temperature of the insulating material 22 in the present embodiment. As shown in FIG. 7A, before the heating step, the conductive particles 21 has a particle size which is defined as a diameter of the conductive particles 21 can be ranged between 5 µm to 50 µm. The shortest distance between two electrodes 31 and 32 is preferably more than two times the particle size of the conductive particles 21. If the dimension of the light-emitting unit 3 is less than 150 µm×150 µm, for example 120 µm×120 µm, 100 µm×100 µm, or 80 µm×80 µm, the shortest distance of two electrodes 31 and 32 of the light-emitting unit 3 is preferably not more than 100 um, for example, not more than 80 um, 50 um, or 40 um.

As shown in FIG. 7B, the conductive particles 21 located in the conductive portion 23 is a bulk and covers at least one of the side surfaces of the electrodes 31, 32 and the conductive pad 14. The external power can empower the light-emitting unit 3 through the conductive pad 14, the conductive particles 21, and the electrodes 31, 32. The conductive particle 21 in the non-conductive portion 24 is granular and enclosed by the insulating material 22. Hence, the current cannot pass through the non-conductive portion 24. The insulating material 22 filled can enhance the joint strength between the light-emitting unit 3 and the carrier 1. The paste 2 has an outmost surface 25 with a curved shape and extends from the carrier 1 to the side surface 34 of the light-emitting unit 3. The shape of the paste 2 is changed after the heating step (compare to FIG. 7A), i.e. the paste 2 has different shapes before and after the heating step. The paste 2 covers a portion of the side surface 34 of the light-emitting unit 3. In more specific, the outmost surface 25 of the paste 2 has an angle θ with respect to the carrier 1. The angle θ gradually increases along the outmost surface 25 toward the side surface 34 of the light-emitting unit 3.

FIG. 8 shows a partial cross-sectional view of the light-emitting module in accordance with another embodiment of the present disclosure. The light-emitting module 300 is configured to emit the light for therapy similar to the light-emitting module 100. The light-emitting module 300 includes a carrier 1, a plurality of light-emitting units 3, a protection layer 4, and a connecting structure (not shown). The carrier 1 includes a lighting portion and the extending portion (not shown). The extending portion of the carrier 1 and the connecting structure can refer to the aforementioned descriptions related to light-emitting module 100. The plurality of light-emitting units 3 is disposed on the same side of the carrier 1. The carrier 1 is flexible and transparent to the light emitted from the light-emitting unit 3. The material of the carrier 1 can refer to aforementioned descriptions related to light-emitting module 100. Structure and the material of the light-emitting unit 3 can be referred to the aforementioned paragraphs. The bonding methods can be referred to aforementioned descriptions related to FIG. 3A~3D.

The protection layer 4 can cover and protects the plurality of light-emitting units from damage caused by the ambient environment. As shown in FIG. 8, the protection layer 4 includes two portions which include the plurality of inner layers 42 and the outer layer 43. The plurality of inner layers 42 is separated from each other. Each inner layer 42 can cover one or more light-emitting units 3 (only one light-emitting unit is shown in FIG. 8). The inner layer 42 has a dome shape to cover the top surface and the side surface of the light-emitting unit 3. The outer layer 43 continuously covers the outmost surfaces of inner layers 42. The refractive index of the inner layer 42 is different from and larger than the refractive index of the outer layer 43. The difference of the refractive indices between the inner layer 42 and the outer layer 43 can cause internal reflection at the interface of the inner layer 42 and the outer layer 43. Hence, a portion of the light emitted from the light-emitting unit 3 can move along a direction substantially parallel to the carrier. Hence, the light-emitting angle of the light-emitting unit 3 or the light-emitting module 300 is larger than that of the light-emitting module which does not have the separated inner layers 42 embedded in the protection layer 4. The light-emitting module 300 can use less numbers of the light-emitting units while having a light-emitting area with a similar brightness level. In an embodiment, the refractive index of the inner layer 42 is more than 1.5, for example 1.53, and the refractive index of the outer layer 43 is less than 1.5, for example 1.4.

The inner layer 42 also provides a better joint strength between the light-emitting unit 3 and the carrier 1. The inner layer 42 has a hardness larger than that of the outer layer 43. The hardness can be measured by the Shore durometer utilizing a hardness test method such as ASTM D-2240. For example, the inner layer 42 has a hardness of D65 measured by the Shore D durometer, and outer layer 43 has a hardness of A30 measured by the Shore A durometer. The outer layer 43 of the protection layer 4 is preferably made of biomedical material which can be referred to aforementioned paragraphs. The inner layers 42 can be made of a transparent encapsulating material aforementioned in the above, such as sections related to light-emitting module 100.

As shown in FIG. 8, the light-emitting angle in x-z plane or y-z plane of the light-emitting unit 3 covered by the protection layer 4 can be varied along the thickness of the inner layer 42 and the outer layer 43. d1 is a distance between the topmost of the inner layer 42 and the top surface of the light-emitting unit 3. The light-emitting angle can be measured from the luminous distribution curve and is defined as the angular range from the maximum light intensity down to 50% of the maximum light intensity. The detailed descriptions of the light-emitting angle can refer to Taiwan Application Serial Number 104103105 and be incorporated herein by reference.

FIG. 9A shows a comparison table of the light-emitting angle of light-emitting unit 3 shown in FIG. 9B~9D with different types of the protection layer 4. The light-emitting unit in case A is not covered by the protection layer, the light-emitting angle of the light-emitting unit 3 in x-z plane or y-z plane, refer to FIG. 9B~9D, is about 120 degree. The light-emitting unit 3 in case B is covered by a single layer of the protection layer shown in FIG. 9B, the light-emitting angle of the light-emitting unit 3 in x-z plane or y-z plane is about 130 degree which is larger than the angle in case A. The light-emitting angles of the light-emitting units 3 shown in FIG. 9C and FIG. 9D can be referred to the numbers of Case C and Case D in FIG. 9A, respectively. The light-emitting units 3 in case C and case D are sequentially covered by the dome shaped inner layer 42 and the outer layer 43. The distance d1 shown in FIG. 9C is about 0.5 mm. The light-emitting angle of the light-emitting unit 3 in FIG. 9C is about 140 degree which is larger than the angle in case B. The distance d1 shown in FIG. 9C is about 0.3 mm, the light-emitting angle of the light-emitting unit 3 is about 150 degree which is even larger than the angle in case C. The distance d1 shown in FIG. 9D is smaller than the distance d1 shown in FIG. 9C. The maximum distance between the outmost side surface of the inner layer 42 and the side surface of the light-emitting unit 3 is larger than the maximum distance between the topmost surface of the inner layer 42 and the top surface of the light-emitting unit 3. The distance d2 between the topmost surface of the inner layer 42 and the outer layer 43 is larger than the distance d1.

Figure 10:
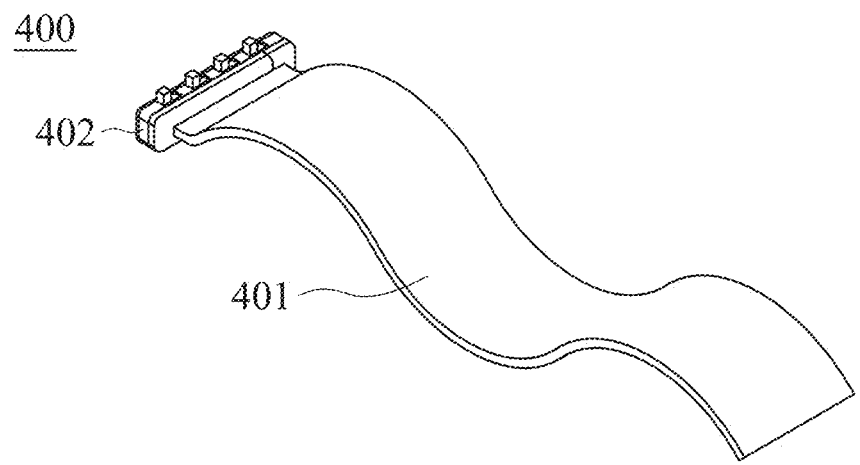
FIG. 10 shows a light-emitting module in accordance with an embodiment of the present disclosure.

FIG. 10 shows a drawing of a light-emitting module in accordance with another embodiment of the present disclosure. The light-emitting module 400 includes a light source module 402 and a light guide film 401 which emits a light. The light is emitted from the light source module 402 toward a side surface of the light guide film 401. The light moving into the light guide film has a portion of light reflected at the interface and propagating in the light guide film and a portion of light exiting the light guide film from the outer surface. The light guide film 401 is flexible and transparent to the light emitted from the light source module 402. The light emitted from the light guide film 401 has uniform illumination. The illumination variation of one side of the light guide film 401 is less than ±20%, for example ±10%. The illumination variation of the opposite side of the light guide film 401 is less than ±10%, for example ±5%. The definition of the illumination variation can refer to aforementioned descriptions of the light-emitting module 100. The light guide film 401 can be made of polymer or oxide. The polymer includes silicone, epoxy, PI, BCB, PFCB, Su8, acrylic resin, PMMA, PET, PC, polyetherimide, or fluorocarbon. The oxide includes $Al_2O_3$, SINR, Su8, or SOG. During the therapy, the outer surface of the light guide film 401 directly or indirectly contacts the treated area (or the photosensitive drug). In an embodiment, the material of the light guide film 401 does not contain hazardous substance or mixture shown in GHS (Globally Harmonized System of Classification and Labelling of Chemicals). The light guide film 401 is preferably made of biomedical material including biomedical grade elastomer, or biomedical grade silicone rubber which causes less or no side effect, for example, skin sensitization ˋ skin corrosion/irritation. In another embodiment, light guide film 401 is a multi-layer structure which includes at least one inner layer and at least one outer layer. The inner layers can be thicker than the outer layers. The inner layer can be made of material(s) selected from polymer or oxide. The outer layer is made of the biomedical material.

Figure 11A:
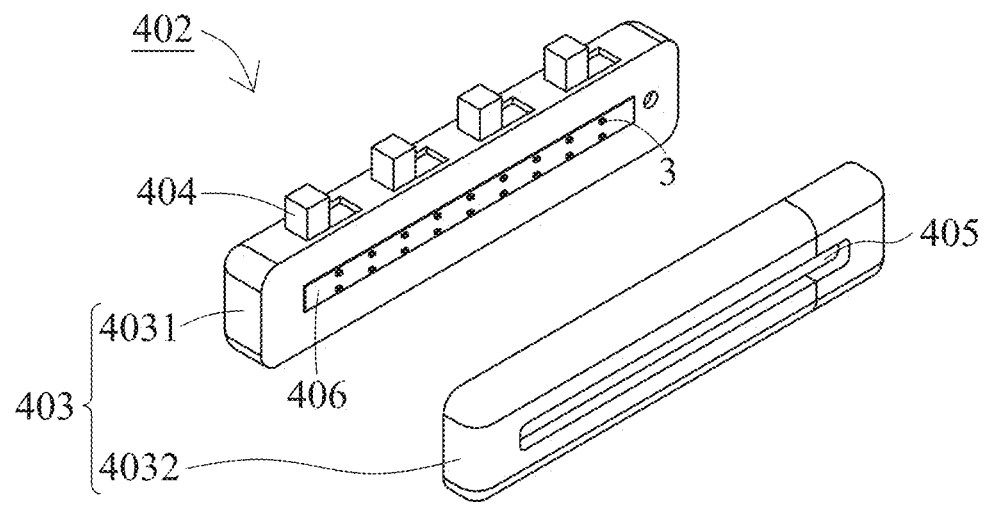
FIG. 11A shows the light source module of the light-emitting module shown in FIG. 10.
Figure 11B:
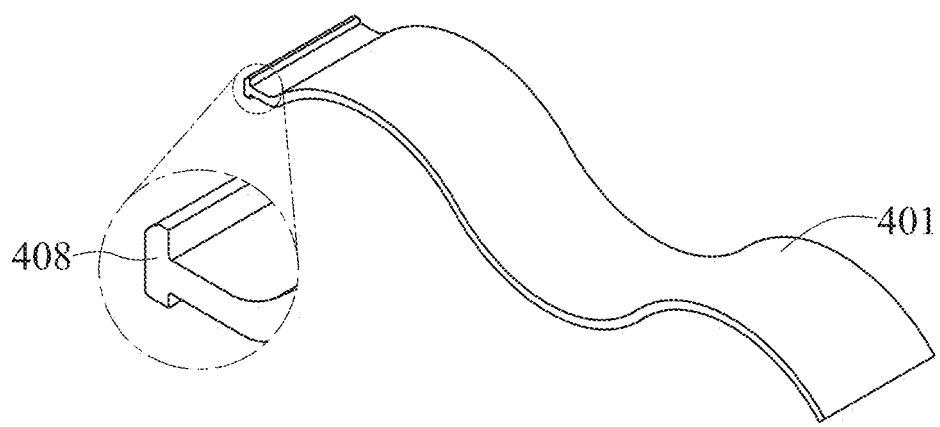
FIG. 11B shows a light guide film of the light-emitting module shown in FIG. 10.

FIG. 11A shows the light source module 402 shown in FIG. 10. The light source module 402 includes a housing 403, a plurality of switches 404, and a light source 406 in the housing 403. The housing includes a first portion 4031 and a second portion 4032. The light source 406 is located in the first portion 4031 and includes a plurality of the light-emitting units 3 disposed on a carrier (not shown), the structure of the light source can refer to aforementioned descriptions shown in FIG. 1C~1D, FIG. 3A~3D, or FIG. 8. The second portion has an opening 405 configured to assemble with the light guide film 401. FIG. 11B shows the light guide film 401 shown in FIG. 10 and being flexible and/or extendable. The light-emitting units 3 are not directly disposed on the light guide film 401. After assembling the light source module 402 and the light guide film 401, the light emitted from the light source 406 can move toward the opening 405 and propagate in the light guide film 401. Since the light source 406 does not directly connect to the light guide film, heat generated from the light-emitting units 3 rarely makes an impact on and/or transfers to the light guide film 401 The light guide film has an outmost surface with a lower temperature such as not burning the treated area of the animal or human after a longer therapy period. Even though the light-emitting module 400 operates for a longer period, the film can still be kept in a relatively lower temperature. Besides, the light guide film 401 is more flexible and has a comfortable touch for treated area. The lighting area of the light guide film 401 is not restricted by the arrangement of the light-emitting units, and the light guide film 401 can have an adjustable length corresponding to size of the treated area. The light guide film 401 can be disposable, or reusable. If the light guide film 401 is reusable, outer surface of the light guide film 401 can be sterilized, cleaned by Alcohol or water after/before one-time use. The light guide film 401 has a connecting portion 408 with a protrusion at end. As shown in the enlarge drawing, the protrusion is extended from the top and the bottom surface of the film 410. The connecting portion 408 is thicker than any other portion of the light guide film 401. In another embodiment, the protrusion portion is only extended from the top surface or the bottom surface of the light guide film 401.

The housing 403 is configured to dissipate the heat generated from the light source 406 and is made of thermal conduction material(s), including conductive material and/or insulating material, for improving heat dissipation. In another embodiment, the housing 403 includes a heat dissipation element, such as a heat sink adjoined to light source 406, to dissipate the heat toward the ambient. The switch 404 is configured to control the light source 406. In more details, the switch 404 can be used to control the luminous intensity, dominant wavelength of the light source 406 according to different requirements of therapy, or/and the amount of powering on of the light-emitting unit 3. The housing 403 can be connected to another control module (not shown) for providing power to light source. In another embodiment, the control module (not shown) can be located within the housing 403.

Figure 12:
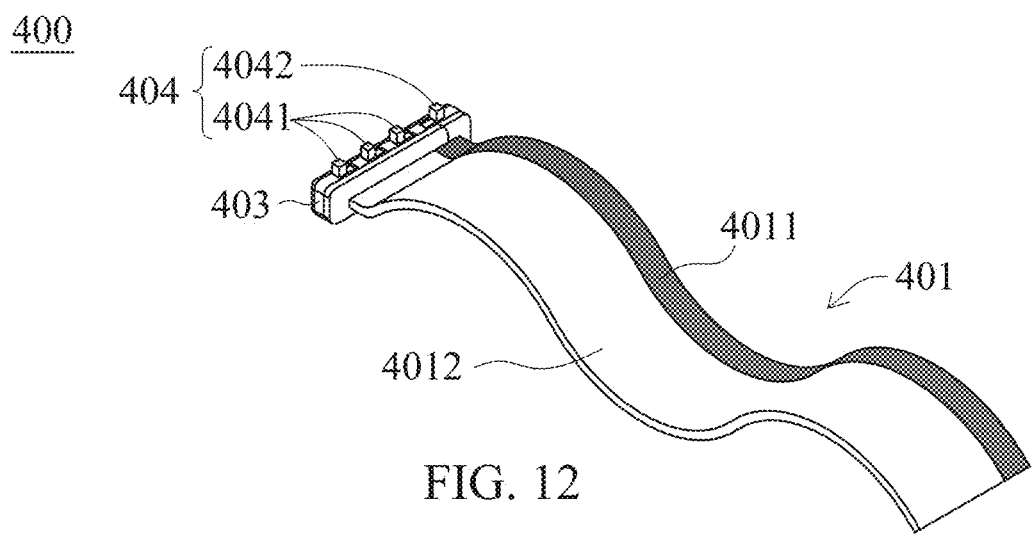
FIG. 12 shows a light-emitting module that emits light in accordance with an embodiment of the present disclosure.

In another embodiment, the switch 404 is configured to control the lighting area of the light guide film 401. FIG. 12 shows a light-emitting module 400 in accordance with an embodiment of the present disclosure. The switch 404 includes a plurality of sub-switches 4041, 4042, and the light guide film 401 includes a plurality of sub-films 4011, 4012. The sub-switches are configured to control the light distribution made in the sub-films. For example, the sub-switch 4042 is used to control the sub-light guide film 4011, and the sub-switches 4041 are used to control the sub-light guide film 4012. If the sub-switch 4042 is turned on and the sub-switches 4041 is turned off, the sub-light guide film 4011 is bright and sub-light guide film 4012 is dark. The sub-light guide film 4011 is lightened by a portion of light-emitting units within the light source 406. The sub-light guide film 4012 may have light leaking out from the sub-light guide film 4011.

Figure 13A:
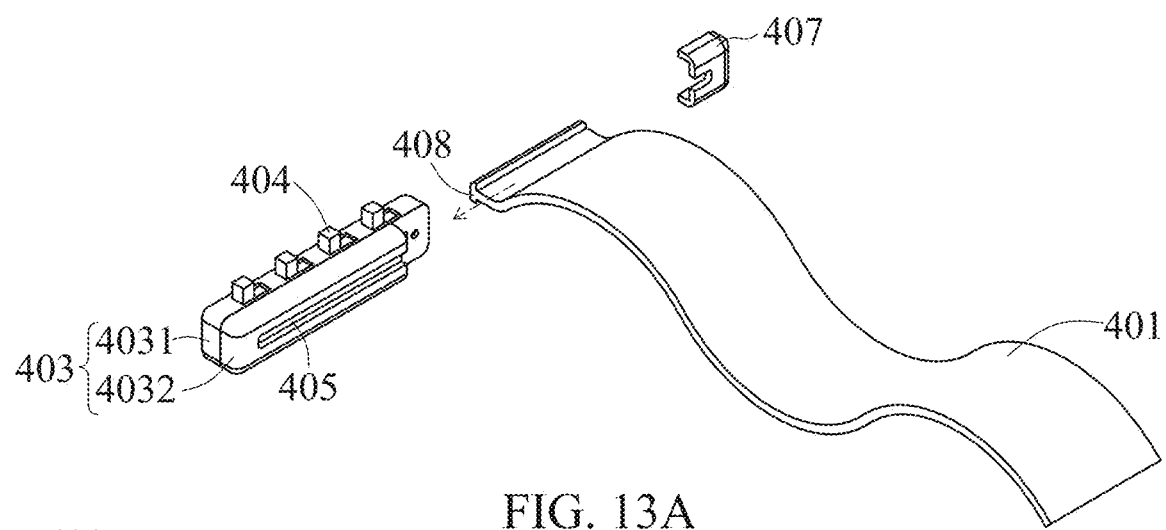
FIGS. 13A~13B show the assembly of the light-emitting module shown in FIG. 10.
Figure 13B:
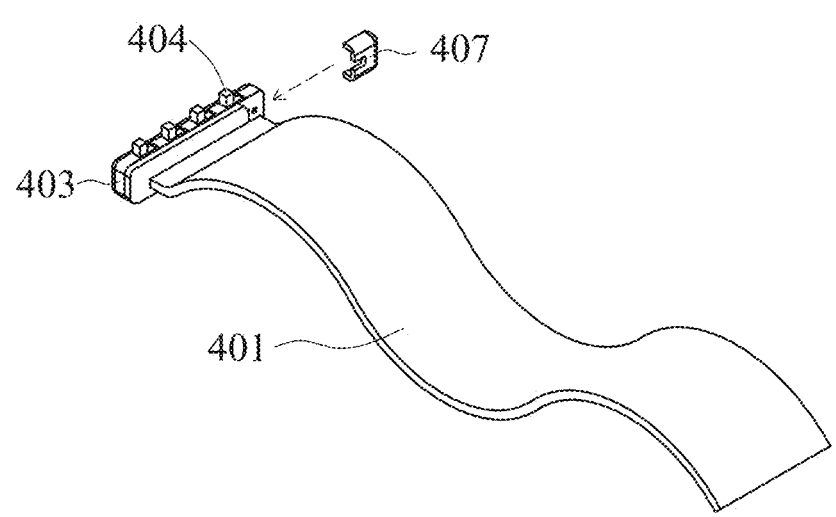

FIG. 13A~13B show the assembling steps of the light-emitting module 400. FIG. 13A shows the light guide film 401 is disassembled from the housing 403. A cap 407 can be assembled from an end of the second portion 4032 of the housing 403 and can be disassembled from the housing 403 for disassembling the light guide film 401. The connecting portion 408 with a protrusion is configure to fix the light guide film 401 after the light guide film 401 sliding into the opening 405. FIG. 13B shows the cap clicked on to fix the light guide film 401 after the light guide film 401 inserting into the housing 403. In another embodiment, the light guide film 401 can be fixed into the housing by clipping without using the cap. In another embodiment (not shown), the light guide film 401 cannot disassemble from and integrated with the housing 403.

Figure 14A:
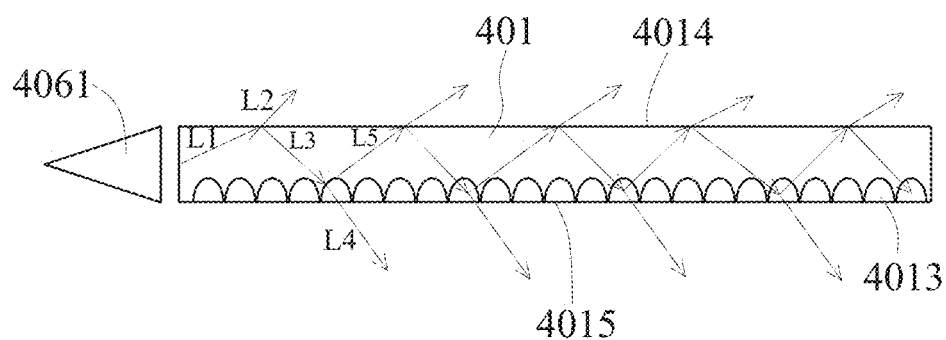
FIG. 14A shows a cross-sectional view of a light guide film in accordance with an embodiment of the present disclosure.
Figure 14B:
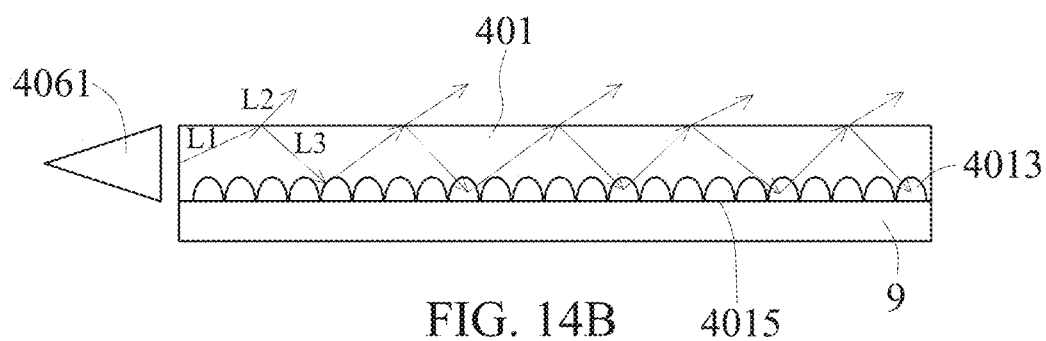
FIG. 14B shows a cross-sectional view of the light guide film in accordance with another embodiment of the present disclosure.

FIG. 14A~14B show the cross-sectional views of the light guide film 401 in accordance with embodiments of the present disclosure. The light guide film 401 includes an optic structure 4013 including a plurality of micro structures with convex formed on the bottom surface 4015 of the light guide film 401. In another embodiment, the micro structure of the optic structure 4013 has concave. In another embodiment, a portion of the micro structure of the optic structure 4013 is formed in a convex and another portion is made in a concave. The optic structure 4013 can be formed by hot press method, injection molding, or silk printing using an ink containing a light scattering material. The light emitted from the light source 406 can be refracted and scattered by the optic structure 4013 and the light can propagate in the light guide film 401 and emit out. FIG. 14A shows a light guide film 401 can emit out the light from double side. The light L1 emits into the light guide film 401 and produces the light L2 and the light L3 at the surface of the light guide film 401. Since the refractive index of the light guide film is different from the air, the light L2 emits out from the top surface 4014 due to refraction and the light L3 emit toward the light guide film 401 due to reflection. While the light L3 emits on the optic structure 4013, the light L3 is scattered to produce the light L4 and reflected to produce the light L5. The light L4 emits out from the bottom surface 4015 of the light guide film 401 and the light L5 emits toward the light guide film 401. Hence, the light guide film 401 can emit light from the top surface 4014 and the bottom surface 4015.

In some therapy case, the light emitted from the light-emitting module only emits toward a direction of the treated area without moving toward opposite direction of the treated area of the human or animal body, such that eliminating the light radiates into the eyes of the treated subject, such as animal or human. FIG. 14B shows a light guide film 401 emits the light only toward the top surface 4014. A reflective layer 9 is formed on the bottom surface 4015 of the light guide film 401. The reflective layer 9 can be made of any reflective material(s). For example, a white pigment and the like can be used in a paste form. The reflective material can be selected from silver (Ag), titanium dioxide ($TiO_2$), zinc oxide (ZnO), barium sulfate ($BaSO_4$), zinc sulfide (ZnS), lead white and antimony oxide ($Sb_2O_3$). The reflective layer 9 can be formed on a back surface of the light guide film 401 by a deposition method, a coating method, a printing method or the like.

Figure 15A:
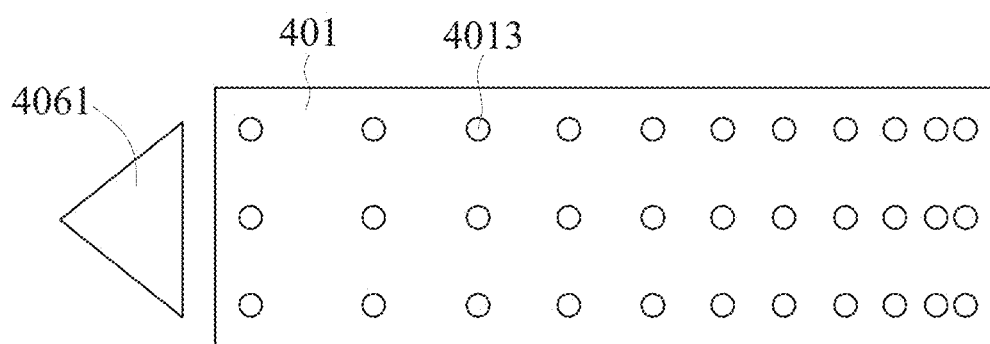
FIG. 15A shows a top view of the light guide film in accordance with an embodiment of the present disclosure.
Figure 15B:
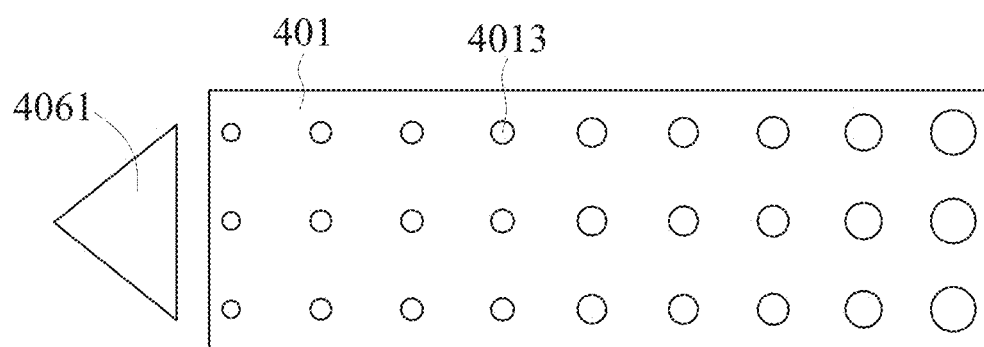
FIG. 15B shows a top view of the light guide film in accordance with another embodiment of the present disclosure.

FIG. 15A~15B show top views of the light guide film 401 in accordance with embodiments of the present disclosure. The light emitted from the light guide film 401 can focus on a region with optic structure 4013 due to the light can be scattered at the position with optic structure 4013. The optic structure 4013 has an arrangement density increasing as the optic structure 4013 goes far away from the light source 4061. Hence, the light emitting surface of the light guide film 401 has a uniform luminous intensity. In details, the emitting surface of the light guide film 401 has a farer area which is far away from the light source 4061 and a closer area which is close to the light source 4061. The amount of light supplied from the light source 4061 decreases by the distance far away the light source 4061. Consequently, the arrangement density of the optic structure 4013 is arranged increasingly by the distance far away the light source 4061. The luminous intensity on the farer area could be enhanced due to the higher arrangement density of the optic structure 4013. Therefore, the luminous intensity of the farer area can be similar to the closer area. The light-emitting surface of the light guide film 401 can have a uniform luminous intensity. As shown in FIG. 15A~15B, the optic structure 4013 includes a plurality of the micro structure. The arrangement density of the optic structure 4013 can be controlled by adjusting an interval of the micro structure of the optic structure 4013. The arrangement density of the optic structure 4013 can be controlled by adjusting the pitch of the adjacent micro structure. FIG. 15A shows the pitch of the adjacent micro structures decreases by the distance the optic structure 4013 goes away from the light source 4061. Besides, the arrangement density of the optic structure can be controlled by adjusting the size of the micro structure. As shown in FIG. 15B, the size of the micro structure of the optic structure 4013 increases as the optic structure 4013 goes away from the light source 4061. In another embodiment, the optic structure 4013 can be formed by combining the interval adjustment and the size adjustment. The shapes of the patterns are not limited to a particular shape, such as round, triangle, rectangle, prisms, curved profiles, polygon or any combination thereof.

Figure 16:
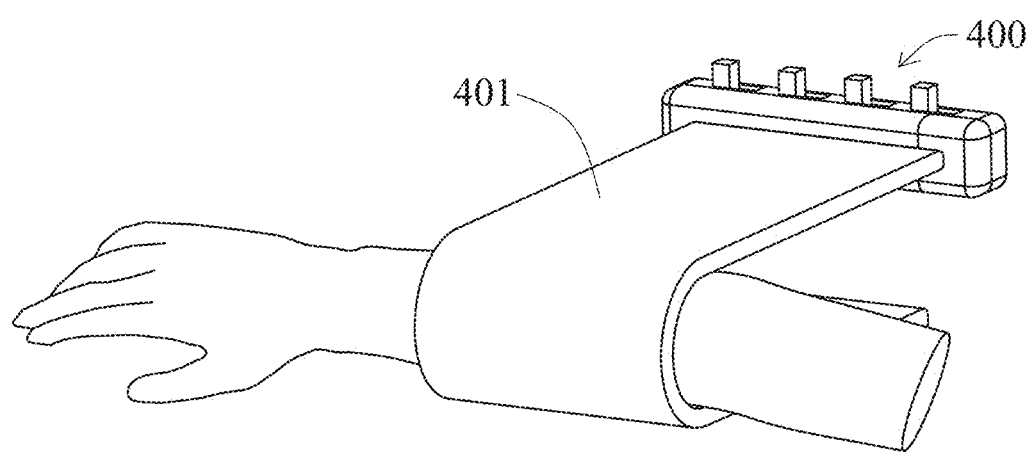
FIG. 16 shows a status that a light-emitting module wrapping on an arm.

FIG. 16 shows an example of a light-emitting module 400 used for therapy. The light guide film 401 wraps the treated area of a treated subject, such as an arm of human, for therapy. The light guide film 401 can be fixed on the arm by the hook and loop fastener or adhere to the treated area through the photosensitive drug which is adhesive. The light-emitting module is light and compact, hence the treated subject, such as human or animal can move freely during therapy.

It will be apparent to those having ordinary skill in the art that various modifications and variations can be made to the devices in accordance with the present disclosure without departing from the scope or spirit of the disclosure. In view of the foregoing, it is intended that the present disclosure covers modifications and variations of this disclosure provided they fall within the scope of the following claims and their equivalents.

What is claimed is:
1. A therapeutic light-emitting module, comprising:
 a housing, comprising:
  a plurality of light-emitting units arranged in a matrix configuration; and
  a switch electrically connected to the plurality of light-emitting units;
  a transparent flexible film comprising a coupling surface, a top surface, and a bottom surface, detachably coupled to the housing with the coupling surface, and configured to receive and propagate light from the plurality of light-emitting units; and
  a protection portion covering the plurality of light-emitting units;
  wherein a portion of the light is emitted from both of the top surface and the bottom surface.
2. The therapeutic light-emitting module according to claim 1, wherein the transparent flexible film is configured to contact a portion of human body.
3. The therapeutic light-emitting module according to claim 1, wherein the transparent flexible film comprises a plurality of textured patterns.
4. The therapeutic light-emitting module according to claim 3, wherein the plurality of textured patterns is formed in a shape of round, triangle, rectangle, prism, curved profile, polygon or any combination thereof.
5. The therapeutic light-emitting module according to claim 1, wherein the housing comprises a first portion and a second portion, and the plurality of light-emitting units is disposed on the first portion.
6. The therapeutic light-emitting module according to claim 5, wherein the transparent flexible film is assembled with the second portion.
7. The therapeutic light-emitting module according to claim 1, wherein the matrix configuration of the plurality of light-emitting units has a dimension less than 150 μm×150 μm.
8. The therapeutic light-emitting module according to claim 1, wherein the protection portion is transparent to light from the plurality of light-emitting units.
9. The therapeutic light-emitting module according to claim 1, wherein the transparent flexible film is made of biomedical material.

10. The therapeutic light-emitting module according to claim 9, wherein the transparent flexible film comprises a biomedical grade elastomer, or a biomedical grade silicone rubber.

* * * * *